United States Patent
Ohkuma et al.

(10) Patent No.: US 9,328,079 B2
(45) Date of Patent: May 3, 2016

(54) PROCESS FOR PRODUCING OPTICALLY ACTIVE AMINE

(71) Applicant: TAKASAGO INTERNATIONAL CORPORATION, Tokyo (JP)

(72) Inventors: Takeshi Ohkuma, Sapporo (JP); Noriyoshi Arai, Sapporo (JP); Kazuhiko Matsumura, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/421,481

(22) PCT Filed: Sep. 6, 2013

(86) PCT No.: PCT/JP2013/074109
§ 371 (c)(1),
(2) Date: Feb. 13, 2015

(87) PCT Pub. No.: WO2014/038666
PCT Pub. Date: Mar. 13, 2014

(65) Prior Publication Data
US 2015/0210657 A1    Jul. 30, 2015

(30) Foreign Application Priority Data

Sep. 7, 2012  (JP) ................................. 2012-197246

(51) Int. Cl.
| | | |
|---|---|---|
| C07D 279/16 | (2006.01) | |
| C07D 241/42 | (2006.01) | |
| C07D 265/36 | (2006.01) | |
| C07B 53/00 | (2006.01) | |

(52) U.S. Cl.
CPC .............. *C07D 279/16* (2013.01); *C07B 53/00* (2013.01); *C07D 241/42* (2013.01); *C07D 265/36* (2013.01)

(58) Field of Classification Search
CPC ..... C07D 79/16; C07D 241/42; C07D 265/36
USPC ........................................... 544/51, 105, 353
See application file for complete search history.

(56) References Cited

U.S. PATENT DOCUMENTS

| | | |
|---|---|---|
| 2002/0035285 A1 | 3/2002 | Burk et al. |
| 2002/0095056 A1 | 7/2002 | Cobley et al. |
| 2002/0156282 A1 | 10/2002 | Blacker et al. |
| 2013/0041151 A1 | 2/2013 | Nara et al. |
| 2014/0187809 A1 | 7/2014 | Hori et al. |

FOREIGN PATENT DOCUMENTS

| | | |
|---|---|---|
| JP | 2011-246435 A | 12/2011 |
| WO | 98/42643 A1 | 10/1998 |
| WO | 01/94359 A1 | 12/2001 |
| WO | 02/08169 A1 | 1/2002 |
| WO | 2012/137460 A1 | 10/2012 |

OTHER PUBLICATIONS

Yong-Gui Zhou, "Asymmetric Hydrogenation of Heteroaromatic Compounds", Acc. Chem. Res., 2007, pp. 1357-1366, vol. 40, No. 12.
Hans-Ulrich Blaser et al., "Catalytic Asymmetric Hydrogenation of C=N Functions", Organic Reactions, 2009, pp. 1-7, vol. 74.
Duo-Sheng Wang et al., "Asymmetric Hydrogenation of Heteroarenes and Arenes", Chemical Reviews, 2012, pp. 2557-2590, vol. 112.
Christopher J. Cobley et al., "Enantioselective Hydrogenation of Imines Using a Diverse Library of Ruthenium Dichloride(diphosphine)(diamine) Precatalysts", Adv. Synth. Catal., 2003, pp. 195-201, vol. 345, No. 1 & 2.
Jie Qin et al., "Asymmetric Hydrogenation of 2- and 2,3-Substituted Quinoxalines with Chiral Cationic Ruthenium Diamine Catalysts", Organic Letters, 2011, pp. 6568-6571, vol. 13, No. 24.
Kia Gao et al., "Iridium-Catalyzed Asymmetric Hydrogenation of 3-Substituted 2H-1,4-Benzoxazines", Adv. Synth. Catal., 2012, 483-488, vol. 354.
Kazuhiko Matsumura et al., "Chiral Ruthenabicyclic Complexes: Precatalysts for Rapid, Enantioselective, and Wide-Scope Hydrogenation of Ketones", Journal of the American Chemical Society, Jun. 16, 2011, pp. 10696-10699, vol. 133.
Noriyoshi Arai et al., Asymetric Hydrogenation of N-Arylimines Catalyzed by the Xyl-Skewphos/DPEN-Ruthenium (II) Complex, Advanced Synthesis & Catalysis, Jun. 29, 2012, pp. 2089-2095, vol. 354.
Noriyoshi Arai et al., "Asymmetric Hydrogenation of Quinoxalines Catalyzed by Ruthenabicyclic Complex", 24th Banyu Sapporo Symposium, Jul. 7, 2012, p. 7.
International Searching Authority, International Search Report for PCT/JP2013/074109 dated Oct. 8, 2013.

(Continued)

*Primary Examiner* — Porfirio Nazario Gonzalez
(74) *Attorney, Agent, or Firm* — Sughrue Mion, PLLC

(57) ABSTRACT

A process for producing an optically active amine compound, characterized by asymmetrically hydrogenating a prochiral carbon-nitrogen double bond in the presence of a ruthenium complex represented by general formula (1) or (2) (wherein P⌒P represents an optically active diphosphine, X represents an anionic group, and Ar represents an optionally substituted arylene group).

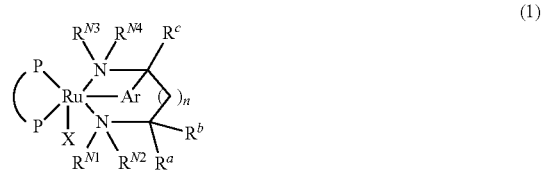

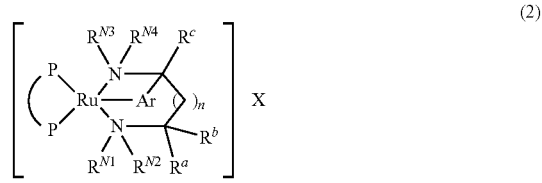

12 Claims, No Drawings

PROCESS FOR PRODUCING OPTICALLY ACTIVE AMINE

CROSS REFERENCE TO RELATED APPLICATIONS

This application is a National Stage of International Application No. PCT/JP2013/074109 filed Sep. 6, 2013, claiming priority based on Japanese Patent Application No. 2012-197246, filed Sep. 7, 2012, the contents of all of which are incorporated herein by reference in their entirety.

TECHNICAL FIELD

The present invention relates to a method for producing an optically active amine compound. Moreover, the present invention relates to a method for producing an optically active amine compound by an asymmetric hydrogenation of a prochiral carbon-nitrogen double bond in the presence of a ruthenium complex having a ruthenabicyclic structure. More specifically, the present invention relates to a novel highly practical method for producing an optically active amine compound, which is useful as a synthetic intermediate of a pharmaceutical.

BACKGROUND ART

As methods for obtaining an optically active amine compound, classical methods have been often used, such as a method in which a naturally-derived amine compound is used, and a method in which a racemic amine compound is synthesized, and then subjected to optical resolution using an optically active organic acid. However, the former method is still disadvantageous in that the raw material substance is difficult to obtain. The latter method is still disadvantageous in that, although the optical purity of the amine compound can be improved by the recrystallization method, the amount of the desired compound cannot exceed the amount present before the optical resolution.

To solve these problems, the synthetic methods based on catalytic asymmetric hydrogenation reactions of prochiral carbon-nitrogen double bonds have been actively studied recently. In recent reviews, methods using complexes having rhodium, iridium, ruthenium, palladium, or titanium as the central metal are described (see Acc. Chem. Res., 2007, vol. 40, p. 1357, Organic Reactions, 2009, vol. 74, p. 1, and Chemical Review, 2012, vol. 112, p. 2557). In these reviews, cases in which rhodium metal or iridium metal, which are expensive, is used are abundant, and, reportedly, optically active amine compounds can be obtained in high yields and with high stereoselectivities. However, it is stated that, since the use of ruthenium metal, which is relatively inexpensive, may result in the loss of the activity of the ruthenium complex due to the produced amine compound in some cases, the application of ruthenium metal to the asymmetric hydrogenation reaction of a carbon-nitrogen double bond is limited, in comparison with the application thereof to the asymmetric hydrogenation reaction of a carbon-oxygen double bond which is applicable to wide varieties of substrates (see Organic Reactions, 2009, vol. 74, p. 1).

Examples of the catalytic asymmetric hydrogenation reaction of a carbon-nitrogen double bond using a ruthenium complex and hydrogen gas are described in the following documents. As for asymmetric hydrogenation reactions of various prochiral imines using $RuCl_2$ (diphosphine) (diamine) and abase, N-(phenylethylidene)aniline, which is an acyclic imine, was asymmetrically hydrogenated with 92% ee at the highest, but the optical purity of 2-methylquinoxaline, which is a cyclic imine, dropped to 69% ee (WO2002/008169 or Adv. Synth. Catal., 2003, vol. 345, p. 195). As for an asymmetric hydrogenation reaction of 2-methylquinoxaline using $RuCl_2[(S)$-hexaphemp$][(S,S)$-dach$]$, only an amine with a moderate optical purity of 81% ee at the highest was obtained (WO2001/094359). As for an asymmetric hydrogenation of 2-methylquinoxaline using Ru(p-cymene) (monosulfonylated diamine) (BArF), an amine with a high optical purity of 98% ee was obtained when the amount of the catalyst was 1 mol %, but the optical purity dropped to 93% ee, when the amount of the catalyst was reduced to 0.1 mol % (Org. Lett., 2011, vol. 13, p. 6568).

Meanwhile, there is a report on a case of an asymmetric hydrogenation reaction of 3-substituted-2H-1,4-benzoxazine using an Ir-diphosphine complex, but there is no report on a case of using Ru metal, which is relatively inexpensive (Adv. Synth. Catal., 2012, vol. 354, p. 483).

SUMMARY OF INVENTION

The present invention has been made in view of the above-described problems, and an object of the present invention is to provide a method for producing an optically active amine based on a catalytic asymmetric synthesis method which achieves a high efficiency and a high enantiomeric excess in producing an optically active amine useful as a synthetic intermediate for a pharmaceutical, an agricultural chemical, or a physiologically active substance.

The present inventors have conducted intensively study to achieve the above-described object, and consequently have developed a method for obtaining an optically active amine with a higher activity and a higher selectivity than those using conventional catalysts, by using a ruthenium complex having a ruthenabicyclic structure as a catalyst in an asymmetric reduction reaction of a prochiral carbon-nitrogen double bond.

Specifically, the present invention provides a method for producing an optically active amine based on an asymmetric reduction using a ruthenium complex having a ruthenabicyclic structure.

The present invention includes the following contents [1] to [6].

[1] A method for producing an optically active amine, comprising:

performing an asymmetric hydrogenation of a prochiral carbon-nitrogen double bond in the presence of a ruthenium complex represented by the following general formula (1) or (2):

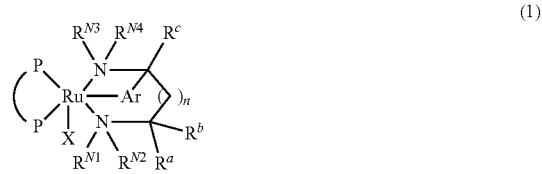

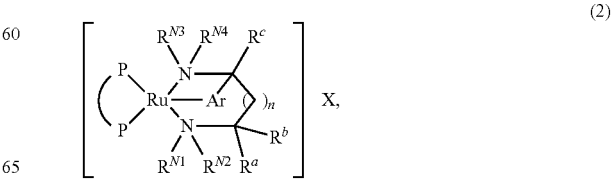

wherein ⌢P represents an optically active diphosphine; X represents an anionic group; $R^a$, $R^b$, and $R^c$ each independently represent a hydrogen atom, an optionally substituted $C_1$ to $C_{20}$ alkyl group, an optionally substituted $C_2$ to $C_H$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; $R^{N1}$ and $R^a$ may together form an optionally substituted alkylene group; n represents an integer of 0 to 3; and Ar represents an optionally substituted arylene group.

[2] The production method according to the above-described [1], wherein
the ruthenium complex is represented by the following general formula (3) or (4):

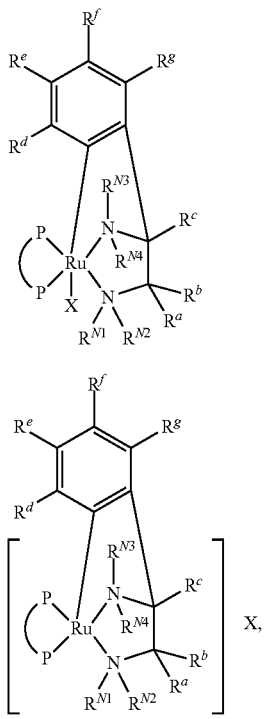

wherein P⌢P represents an optically active diphosphine; X represents an anionic group; $R^a$, $R^b$, and $R^c$ each independently represent a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^d$, $R^e$, $R^f$, and $R^g$ each independently represent a hydrogen atom, an optionally substituted $C_1$ to $C_{20}$ alkyl group, a $C_1$ to $C_5$ halogenated alkyl group, a halogen atom, an optionally substituted aryl group, an optionally substituted $C_3$ to $C_8$ cycloalkyl group, a tri-substituted silyl group, or an optionally substituted $C_1$ to $C_{20}$ alkoxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; and $R^{N1}$ and $R^a$ may together form an optionally substituted alkylene group.

[3] The production method according to the above-described [1] or [2], wherein
the optically active diphosphine represented by ⌢P is a diphosphine represented by the following general formula (5):

$$R^1R^2P\text{-}Q\text{-}PR^3R^4 \quad (5)$$

wherein $R^1$, $R^2$, $R^3$, and $R^4$ each independently represent an optionally substituted aryl group, an optionally substituted cycloalkyl group, or an optionally substituted alkyl group, and the pair of $R^1$ and $R^2$ and/or the pair of $R^3$ and $R^4$ may together form a ring; and Q represents biphenyldiyl, binaphthalenediyl, bipyridinediyl, paracyclophanediyl, or ferrocenediyl group, has an asymmetric structure, and may be substituted.

[4] The production method according to the above-described [3], wherein
the ⌢P is an optically active diphosphine represented by the following general formula (6):

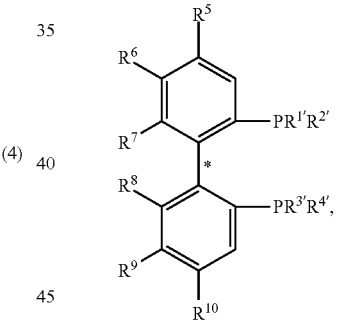

wherein $R^{1'}$, $R^{2'}$, $R^{3'}$, and $R^{4'}$ each independently represent a phenyl group optionally substituted by a substituent(s) selected from the group consisting of alkyl groups having 1 to 4 carbon atoms and alkoxy groups having 1 to 4 carbon atoms; a cyclopentyl group; or a cyclohexyl group; $R^5$, $R^6$, $R^7$, $R^8$, $R^9$, and $R^{10}$ each independently represent a hydrogen atom, an optionally substituted alkyl group having 1 to 4 carbon atoms, an optionally substituted alkoxy group having 1 to 4 carbon atoms, a halogen atom, a halogenated alkyl group having 1 to 4 carbon atoms, or a dialkylamino group, or two of $R^5$, $R^6$, and $R^7$ may together form an optionally substituted alkylene group; an optionally substituted alkylenedioxy group; or an optionally substituted aromatic ring, two of $R^8$, $R^9$, and $R^{10}$ may together form an optionally substituted alkylene group; an optionally substituted alkylenedioxy group; or an optionally substituted aromatic ring, $R^7$ and $R^8$ may together form an optionally substituted alkylene group; an optionally substituted alkylenedioxy group; or an optionally substituted aromatic ring; provided that neither $R^7$ nor $R^8$ is a hydrogen atom; and * indicates axial chirality.

[5] The production method according to the above-described [3] or [4], wherein
$R^1$, $R^2$, $R^3$, and $R^4$ in general formula (5) and $R^{1'}$, $R^{2'}$, $R^{3'}$, and $R^{4'}$ in general formula (6) are 3,5-xylyl groups.

[6] The production method according to any one of the above-described [1] to [5], wherein
the method is conducted in the presence of a base compound.

The present invention makes it possible to produce an optically active amine compound with a high optical purity by using a small amount of the catalyst. The production method of the present invention is extremely industrially useful, because the production method is excellent in terms of the reactivity and the conversion in the asymmetric hydrogenation reaction of a prochiral carbon-nitrogen double bond, and also excellent in terms of enantioselectivity, diastereoselectivity, and the like.

DESCRIPTION OF EMBODIMENTS

Hereinafter, the present invention will be described in detail.

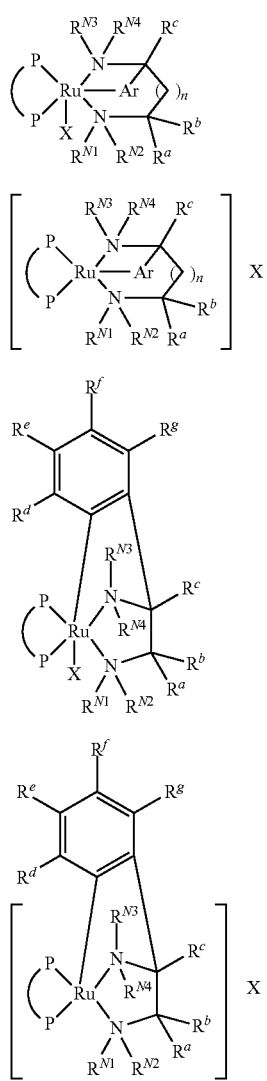

In each of the ruthenium complexes of general formulae (1) and (2), the optionally substituted arylene group represented by Ar may be a monocyclic, polycyclic, or fused-cyclic divalent arylene group having 6 to 36, preferably 6 to 18, and more preferably 6 to 12 carbon atoms or a monocyclic, polycyclic, or fused-cyclic divalent heteroarylene group having a 3 to 8-membered, preferably 5 to 8-membered ring containing 1 to 4, preferably 1 to 3 or 1 to 2 hetero atoms selected from nitrogen atoms, oxygen atoms, and sulfur atoms. Preferred examples of the arylene group include a phenylene group, a naphthalenediyl group, a pyridinediyl group, a thiophenediyl group, a furandiyl group, and the like. The arylene group is particularly preferably a phenylene group. The positions at which the divalent arylene group is bound are not particularly limited, and are preferably the positions of two adjacent carbon atoms (positions ortho to each other). In addition, the substituent(s) attached to the arylene group include linear or branched alkyl groups, linear or branched alkoxy groups, cycloalkyl groups, halogen atoms, aryl groups, heteroaryl groups, tri-substituted silyl groups, and the like, and are preferably linear or branched alkoxy groups.

The substituents attached to the arylene group are described below.

Examples of the linear or branched alkyl groups include linear or branched alkyl groups having 1 to 10, preferably 1 to 6, and more preferably 1 to 4 carbon atoms, and the alkyl groups may be substituted by a halogen atom(s) such as fluorine atoms. Specific examples of the alkyl groups include methyl groups, ethyl groups, n-propyl groups, isopropyl groups, n-butyl groups, isobutyl groups, s-butyl groups, t-butyl groups, trifluoromethyl groups, and the like.

Examples of the linear or branched alkoxy groups include linear or branched alkoxy groups having 1 to 10, preferably 1 to 6, and more preferably 1 to 4 carbon atoms, and specific examples thereof include methoxy groups, ethoxy groups, n-propoxy groups, isopropoxy groups, n-butoxy groups, s-butoxy groups, isobutoxy groups, t-butoxy groups, and the like. Methoxy groups are preferable.

The cycloalkyl groups include saturated or unsaturated monocyclic, polycyclic, or fused-cyclic cycloalkyl groups having 3 to 15 and preferably 5 to 7 carbon atoms, and specifically include cyclopentyl groups, cyclohexyl groups, and the like. The ring of each of these cycloalkyl groups may be substituted by one of or two or more of alkyl groups having 1 to 4 carbon atoms and alkoxy groups having 1 to 4 carbon atoms.

The halogen atoms include chlorine atoms, bromine atoms, iodine atoms, fluorine atoms, and the like.

Examples of the aryl groups include aryl groups having 6 to 14 carbon atoms, and specific examples thereof include phenyl groups, naphthyl groups, anthryl groups, phenanthryl groups, biphenyl groups, and the like. These aryl groups may have one or two or more substituents, and the substituents include the above-described alkyl groups having 1 to 4 carbon atoms and alkoxy groups having 1 to 4 carbon atoms, and the like.

The heteroaryl groups include 5-membered or 6-membered cyclic groups containing oxygen atoms, sulfur atoms, nitrogen atoms, and the like, and specifically include furyl groups, thienyl groups, pyridyl groups, and the like.

The tri-substituted silyl groups include silyl groups tri-substituted by the above-described alkyl groups or aryl groups, and examples thereof include trimethylsilyl groups, triethylsilyl groups, triisopropylsilyl groups, tert-butyldimethylsilyl groups, diphenylmethylsilyl groups, dimethylphenylsilyl groups, and the like.

In each of the ruthenium complexes represented by general formulae (1), (2), (3), and (4) of the present invention, the anionic group represented by X may be H; a halogen atom such as Cl, Br, or I; a complex anion such as $BH_4$, $BF_4$, $BPh_4$, $PF_6$, an acetoxy group, or a trifluoromethanesulfonyloxy group; or the like. Of these, the anionic group is preferably a halogen or a trifluoromethanesulfonyloxy group, and particularly preferably Cl.

The groups represented by $R^a$, $R^b$, $R^e$, $R^d$, $R^e$, $R^f$, $R^g$, $R^{N1}$, $R^{N2}$, $R^{N3}$, and $R^{N4}$ in each of the ruthenium complexes represented by general formulae (1), (2), (3), and (4) of the present invention are described below.

The $C_1$ to $C_{20}$ alkyl group may be a linear or branched alkyl group having 1 to 20, preferably 1 to 5, and more preferably 1 to 4 carbon atoms, and examples thereof include a methyl group, an ethyl group, a n-propyl group, an isopropyl group, a n-butyl group, an isobutyl group, a s-butyl group, a t-butyl group, a n-pentyl group, a n-hexyl group, a decyl group, a dodecyl group, a hexadecyl group, and the like.

The $C_2$ to $C_{20}$ alkenyl group may be a linear or branched alkenyl group having 2 to 20, preferably 2 to 10, and more preferably 2 to 6 carbon atoms, and example thereof include an ethenyl group, a n-propenyl group, an isopropenyl group, a 1-butenyl group, a 1-buten-2-yl group, a pentenyl group, a hexenyl group, and the like.

The $C_1$ to $C_{20}$ alkoxy group may be a group in which an oxygen atom is bound to any of the above-described linear or branched alkyl groups having 1 to 20, preferably 1 to 5, and more preferably 1 to 4 carbon atoms. Examples of the alkoxy group include a methoxy group, an ethoxy group, a n-propoxy group, an isopropoxy group, a n-butoxy group, a s-butoxy group, an isobutoxy group, a t-butoxy group, and the like.

The halogenated alkyl group having 1 to 5 carbon atoms may be a trifluoromethyl group, a pentafluoroethyl group, a heptafluoropropyl group, a trichloromethyl group, or the like.

The $C_3$ to $C_8$ cycloalkyl group may be a saturated or unsaturated monocyclic, polycyclic, or fused-cyclic cycloalkyl group having 3 to 8 and preferably 5 to 7 carbon atoms. Examples of the cycloalkyl group include a cyclopropyl group, a cyclopentyl group, a cyclohexyl group, and the like.

The halogen atom may be a chlorine atom, a bromine atom, a fluorine atom, or the like.

The tri-substituted silyl group may be a silyl group tri-substituted by the above-described alkyl groups or aryl groups, and examples thereof include a trimethylsilyl group, a triethylsilyl group, a triisopropylsilyl group, a t-butyldimethylsilyl group, a diphenylmethylsilyl group, a dimethylphenylsilyl group, and the like.

The $C_7$ to $C_{20}$ aralkyl group may be an aralkyl group having 7 to 20, preferably 7 to 15 carbon atoms or 7 to 10 carbon atoms in which any of the above-described alkyl groups having 1 to 14 carbon atoms is bound to a monocyclic, polycyclic, or fused-cyclic aryl group having 6 to 19 and preferably 6 to 14 carbon atoms. Examples of the aralkyl group include a benzyl group, an α-methylbenzyl group, an α,α-dimethylbenzyl group, a 2-phenylethyl group, a 3-phenylpropyl group, and the like.

In addition, the substituents attached to the above-described $C_1$ to $C_{20}$ alkyl group, $C_2$ to $C_{20}$ alkenyl group, $C_1$ to $C_{20}$ alkoxy group, halogenated alkyl group, $C_3$ to $C_8$ cycloalkyl group, tri-substituted silyl group, and $C_7$ to $C_{20}$ aralkyl group include the linear or branched alkyl groups, linear or branched alkoxy groups, cycloalkyl groups, halogen atoms, aryl groups, heteroaryl groups, tri-substituted silyl groups, and the like, as described above in the description of the arylene group.

The aryl group of the optionally substituted aryl group may be a monocyclic, polycyclic, or fused-cyclic aryl group having 6 to 20, preferably 6 to 14 or 6 to 12 carbon atoms. Specifically, the aryl group may be a phenyl group, a naphthyl group, an anthryl group, a phenanthryl group, a biphenyl group, or the like, and is preferably a phenyl group. These aryl groups may have one or two or more substituents, and the substituents include alkyl groups having 1 to 4 carbon atoms such as methyl groups, isopropyl groups, and t-butyl groups; alkoxy groups having 1 to 4 carbon atoms such as methoxy groups, ethoxy groups, n-propoxy groups, isopropoxy groups, n-butoxy groups, isobutoxy groups, s-butoxy groups, and t-butoxy groups; and the like, as described above.

The optionally substituted heterocyclic group may be a saturated or unsaturated 5-membered or 6-membered cyclic group containing oxygen atoms, sulfur atoms, nitrogen atoms, and the like, and is specifically a furyl group, a thienyl group, a pyridyl group, or the like. These heterocyclic groups may have one or two or more substituents, and the substituents include alkyl groups having 1 to 4 carbon atoms such as methyl groups, isopropyl groups, and t-butyl groups; alkoxy groups having 1 to 4 carbon atoms such as methoxy groups, ethoxy groups, n-propoxy groups, isopropoxy groups, n-butoxy groups, isobutoxy groups, s-butoxy groups, and t-butoxy groups; and the like, as described above.

Meanwhile, the alkylene group formed by $R^b$ and $R^c$ may be a linear or branched alkylene group having 1 to 6 and preferably 1 to 4 carbon atoms. Examples of the alkylene group include a methylene group, an ethylene group, a trimethylene group, a propylene group, a tetramethylene group, and the like. These alkylene groups may be substituted by alkyl groups having 1 to 4 carbon atoms, alkoxy groups having 1 to 4 carbon atoms, and halogen atoms.

The alkylenedioxy group formed by $R^b$ and $R^c$ may be a linear or branched alkylenedioxy group having 1 to 6 and preferably 1 to 4 carbon atoms. Examples of the alkylenedioxy group include a methylenedioxy group, an ethylenedioxy group, a trimethylenedioxy group, and the like. These alkylenedioxy groups may be substituted by alkyl groups having 1 to 4 carbon atoms, alkoxy groups having 1 to 4 carbon atoms, and halogen atoms.

The alkylene group formed by $R^{N1}$ and $R^a$ may be a linear or branched alkylene group having 1 to 6 and preferably 1 to 4 carbon atoms. Examples of the alkylene group include a methylene group, an ethylene group, a trimethylene group, a propylene group, a tetramethylene group, and the like. These alkylene groups may be substituted by alkyl groups having 1 to 4 carbon atoms, alkoxy groups having 1 to 4 carbon atoms, and halogen atoms.

In each of the ruthenium complexes represented by general formulae (1), (2), (3), and (4) of the present invention, the optically active diphosphine represented by P⌒P is not particularly limited, as long as the diphosphine can be coordinated to ruthenium. Examples of the optically active diphosphine include those represented by the following general formula (5):

$$R^1R^2P\text{-}Q\text{-}PR^2R^4 \tag{5}$$

wherein $R^1$, $R^2$, $R^3$, and $R^4$ each independently represent an optionally substituted aryl group, an optionally substituted cycloalkyl group, or an optionally substituted alkyl group, and the pair of $R^1$ and $R^2$ and/or the pair of $R^3$ and $R^4$ may together form a ring; and Q represents biphenyldiyl, binaphthalenediyl, bipyridinediyl, paracyclophanediyl, or ferrocenediyl group, has an asymmetric structure, and may be substituted.

Examples of the optionally substituted aryl group represented by each of $R^1$, $R^2$, $R^3$, and $R^4$ in the above-described formula include aryl groups having 6 to 14 carbon atoms, and specific examples thereof include a phenyl group, a naphthyl group, an anthryl group, a phenanthryl group, a biphenyl group, and the like.

These aryl groups may have one or two or more substituents, and the substituents include alkyl groups, alkoxy groups, and the like.

The alkyl groups serving as the substituents of the aryl group include linear or branched alkyl groups having, for example, 1 to 15, preferably 1 to 10, and more preferably 1 to 6 carbon atoms, and specific examples thereof include methyl groups, ethyl groups, n-propyl groups, isopropyl groups, n-butyl groups, s-butyl groups, isobutyl groups, t-butyl groups, and the like.

The alkoxy groups serving as the substituents of the aryl group include linear or branched alkoxy groups having, for example, 1 to 6 carbon atoms, and specifically include methoxy groups, ethoxy groups, n-propoxy groups, isopropoxy groups, n-butoxy groups, s-butoxy groups, isobutoxy groups, t-butoxy groups, and the like.

In addition, the optionally substituted cycloalkyl group represented by each of $R^1$, $R^2$, $R^3$, and $R^4$ may be a cycloalkyl group having a 5-membered or 6-membered ring, and preferred cycloalkyl groups include a cyclopentyl group, a cyclohexyl group, and the like. The ring of each of these cycloalkyl groups may be substituted by one of or two or more of substituents such as the alkyl groups or alkoxy group listed as the substituents of the aryl group.

The optionally substituted alkyl group may be a linear or branched alkyl group having, for example, 1 to 15, preferably 1 to 10, and more preferably 1 to 6 carbon atoms, and specific examples thereof include a methyl group, an ethyl group, a n-propyl group, an isopropyl group, a n-butyl group, a s-butyl group, an isobutyl group, a t-butyl group, and the like. These alkyl groups may be substituted by one of or two or more of substituents such as the alkoxy groups listed as the substituents of the aryl group.

Meanwhile, the ring which may be formed by the pair of $R^1$ and $R^2$ and/or the pair of $R^3$ and $R^4$ may be a four-membered, five-membered, or six-membered optically active ring, as a ring including the phosphorus atom to which $R^1$ and $R^2$ or $R^3$ and $R^4$ are bound. Specific rings include a phosphetane ring, a phosphinane ring, a phosphane ring, a 2,4-dimethylphosphetane ring, a 2,4-diethylphosphetane ring, a 2,5-dimethylphospholane ring, a 2,5-diethylphospholane ring, a 2,6-dimethylphosphinane ring, a 2,6-diethylphosphinane ring, and the like.

Meanwhile, Q may be an optionally substituted biphenyldiyl, binaphthalenediyl, bipyridinediyl, paracyclophanediyl, or ferrocenediyl group having an asymmetric structure, or the like.

The biphenyldiyl group, binaphthalenediyl group, and bipyridinediyl group are preferably those having a 1,1'-biaryl-2,2'-diyl type structure having an axially chiral structure. The biphenyldiyl group, the binaphthalenediyl group, and the bipyridinediyl group may be substituted by alkyl groups having 1 to 6 carbon atoms such as methyl groups, ethyl groups, n-propyl groups, isopropyl groups, n-butyl groups, s-butyl groups, isobutyl groups, and t-butyl groups; alkoxy groups having 1 to 6 carbon atoms such as methoxy groups, ethoxy groups, n-propoxy groups, isopropoxy groups, n-butoxy groups, s-butoxy groups, isobutoxy groups, and t-butoxy groups; halogen atoms; alkylene groups such as methylene groups, ethylene groups, and trimethylene groups; alkylenedioxy groups such as methylenedioxy groups, ethylenedioxy groups, and trimethylenedioxy groups; hydroxyl groups; amino groups; substituted amino groups; and the like.

The paracyclophanediyl group may be substituted by the above-described alkyl groups, alkoxy groups, alkylenedioxy groups such as methylenedioxy groups, ethylenedioxy groups, and trimethylenedioxy groups, hydroxyl groups, amino groups, and substituted amino groups.

The ferrocenediyl group may also have a substituent(s), and the substituents include the above-described alkyl groups, alkoxy groups, alkylenedioxy groups, hydroxyl groups, amino groups, substituted amino groups, and the like.

The substituted amino groups include amino groups substituted by one or two alkyl groups having 1 to 6 carbon atoms.

Specific examples of the optically active diphosphine represented by general formula (5) include known optically active diphosphines, and a preferred example thereof is a compound represented by the following general formula (6).

An optically active diphosphine represented by

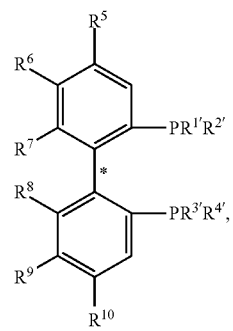

(6)

wherein $R^{1'}$, $R^{2'}$, $R^{3'}$, and $R^{4'}$ each independently represent a phenyl group optionally substituted by a substituent(s) selected from the group consisting of alkyl groups having 1 to 4 carbon atoms and alkoxy groups having 1 to 4 carbon atoms; a cyclopentyl group; or a cyclohexyl group; $R^5$, $R^6$, $R^7$, $R^8$, $R^9$, and $R^{10}$ each independently represent a hydrogen atom, an optionally substituted alkyl group having 1 to 4 carbon atoms, an optionally substituted alkoxy group having 1 to 4 carbon atoms, a halogen atom, a halogenated alkyl group having 1 to 4 carbon atoms, or a dialkylamino group, or two of $R^5$, $R^6$, and $R^7$ may together form an optionally substituted alkylene group; an optionally substituted alkylenedioxy group; or an optionally substituted aromatic ring, two of $R^8$, $R^9$, and $R^{10}$ may together form an optionally substituted alkylene group; an optionally substituted alkylenedioxy group; or an optionally substituted aromatic ring, $R^7$ and $R^8$ may together form an optionally substituted alkylene group; an optionally substituted alkylenedioxy group; or an optionally substituted aromatic ring, provided that neither $R^7$ nor $R^8$ is a hydrogen atom; and * indicates axial chirality.

The alkyl groups and the alkoxy groups represented by $R^{1'}$, $R^{2'}$, $R^{3'}$, and $R^{4'}$ in general formula (6) include the same alkyl groups and alkoxy groups as described above in the description of the substituents of the aryl groups represented by $R^1$, $R^2$, $R^3$, and $R^4$ of general formula (5). The alkyl groups, alkoxy groups, halogen atoms, alkylene groups, and alkylenedioxy groups represented by $R^5$, $R^6$, $R^7$, $R^8$, $R^9$, and $R^{10}$ in general formula (6) include those described above in the description of the substituents of the biphenyldiyl group represented by Q in general formula (5). The aromatic ring formed by two groups may be a 6-membered aromatic ring formed together with the adjacent atoms. The formed aromatic ring may be substituted by alkyl groups having 1 to 4 carbon atoms, alkoxy groups having 1 to 4 carbon atoms, and the like.

A preferred example of the above-described general formula (6) is as follows. Specifically, for example, $R^{1'}$, $R^{2'}$, $R^{3'}$, and $R^{4'}$ each independently represent a phenyl group optionally substituted by one or multiple substituents selected from the group consisting of alkyl groups having 1 to 4 carbon atoms and alkoxy groups having 1 to 4 carbon atoms; $R^6$ and $R^7$ together form a tetramethylene group; a methylenedioxy group optionally substituted by alkyl groups having 1 to 4 carbon atoms, fluorine atoms, or the like; or a benzene ring together with the adjacent carbon atoms; and $R^8$ and $R^9$ together form a tetramethylene group; a methylenedioxy group optionally substituted by alkyl groups having 1 to 4 carbon atoms, fluorine atoms, or the like; or a benzene ring formed together with adjacent carbon atoms.

Moreover, specific examples of more preferred optically active diphosphines of the present invention include optically active diphosphines represented by the following general formulae (7) and (8):

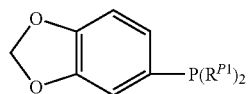
(7)

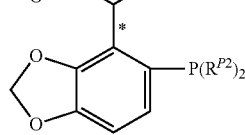

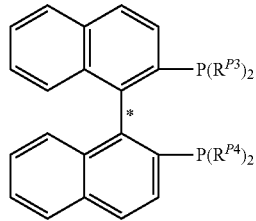
(8)

Specific examples of $R^{P1}$ and $R^{P2}$ in general formula (7) and specific examples of $R^{P3}$ and $R^{P4}$ in general formula (8) include a phenyl group, a p-tolyl group, a m-tolyl group, an o-tolyl group, a 3,5-xylyl group, a 3,5-di-t-butylphenyl group, a p-t-butylphenyl group, a p-methoxyphenyl group, a 3,5-di-t-butyl-4-methoxyphenyl group, a 3,5-dimethyl-4-methoxyphenyl group, a p-chlorophenyl group, a m-chlorophenyl group, a p-fluorophenyl group, a m-fluorophenyl group, and the like.

Specific examples of the optically active diphosphines represented by general formulae (5), (6), (7), and (8) of the present invention include 2,2'-bis(diphenylphosphino)-1,1'-binaphthyl (BINAP), 2,2'-bis[di(p-tolyl)phosphino]-1,1'-binaphthyl (TolBINAP), 2,2'-bis[di(m-tolyl)phosphino]-1,1'-binaphthyl, 2,2'-bis[di(3,5-xylyl)phosphino]-1,1'-binaphthyl (XylBINAP), 2,2'-bis[di(p-t-butylphenyl)phosphino]-1,1'-binaphthyl, 2,2'-bis[di(p-methoxyphenyl)phosphino]-1,1'-binaphthyl, 2,2'-bis[di(3,5-di-t-butyl-4-methoxyphenyl)phosphino]-1,1'-binaphthyl, 2,2'-bis[di(cyclopentyl)phosphino]-1,1'-binaphthyl, 2,2'-bis[di(cyclohexyl)phosphino]-1,1'-binaphthyl, 2,2'-bis(diphenylphosphino)-5,5',6,6',7,7',8,8'-octahydro-1,1'-binaphthyl (H8-BINAP), 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di-3,5-xylylphosphino)-5,5',6,6',7,7',8,8'-octahydro-1,1'-binaphthyl (Xyl-H8-BINAP), 2,2'-bis(di-p-t-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine) (SEGPHOS), (4,4'-bi-1,3-benzodioxole)-5,5'-diyl)bis(di(3,5-xylyl)phosphine) (DM-SEGPHOS), ((4,4'-bi-1,3-benzodioxole)-5,5'-diyl)bis(di(3,5-di-t-butyl-4-methoxyphenyl)phosphine) (DTBM-SEGPHOS), ((4,4'-bi-1,3-benzodioxole)-5,5'-diyl)bis(di(3,5-dimethyl-4-methoxyphenyl)phosphine) (DMM-SEGPHOS), ((4,4'-bi-1,3-benzodioxole)-5,5'-diyl)bis(di(4-methoxyphenyl)phosphine), ((4,4'-bi-1,3-benzodioxole)-5,5'-diyl)bis(dicyclohexylphosphine), ((4,4'-bi-1,3-benzodioxole)-5,5'-diyl)bis(bis(3,5-di-t-butylphenyl)phosphine), 2,2'-bis(di-3,5-xylylphosphino)-6,6'-dimethoxy-1,1'-biphenyl (Xyl-MeO-BIPHEP), 2,2'-bis(diphenylphosphino)-6,6'-dimethyl-1,1-biphenyl (BIPHEP), 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 2,2'-bis(diphenylphosphino)-6,6'-dimethoxy-1,1'-biphenyl (MeO-BIPHEP), 2,2'-bis(di-p-tolylphosphino)-6,6'-dimethoxy-1,1'-biphenyl, 2,2',6,6'-tetramethoxy-4,4'-bis(di-3,5-xylylphosphino)-3,3'-bipyridine (Xyl-P-Phos), 2,2',6,6'-tetramethoxy-4,4'-bis(diphenylphosphino)-3,3'-bipyridine (P-Phos), 2,2',6,6'-tetramethoxy-4,4'-bis(di-p-tolylphosphino)-3,3'-bipyridine, 2,2',6,6'-tetramethoxy-4,4'-bis(di-o-tolylphosphino)-3,3'-bipyridine, 4,12-bis(di-3,5-xylylphosphino)-[2.2]-paracyclophane (Xyl-PHANPHOS), 4,12-bis(diphenylphosphino)-[2.2]-paracyclophane (PHANPHOS), 4,12-bis(di-p-tolylphosphino)-[2.2]-paracyclophane, 4,12-bis(di-o-tolylphosphino)-[2.2]-paracyclophane, 1,1'-bis(2,4-diethylphosphotano)ferrocene, 1,13-bis(diphenylphosphino)-7,8-dihydro-6H-dibenzo[f,h][1,5]dioxonin, 1,13-bis(bis(3,5-dimethylphenyl)phosphino)-7,8-dihydro-6H-dibenzo[f,h][1,5]dioxonin (Xyl-C3-TunePhostunephos), 6,6'-bis(bis(3,5-dimethylphenyl)phosphino)-2,2',3,3'-tetrahydro-5,5'-bi-1,4-benzodioxin (Xyl-SYNPHOS), and the like.

In addition to the above-described diphosphines, specific examples of optically active bisphosphine compounds usable in the present invention include N,N-dimethyl-1-[1',2-bis(diphenylphosphino)ferrocenyl]ethylamine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis[(o-methoxyphenyl)phenylphosphino]ethane, 1,2-bis(2,5-dimethylphospholano)ethane, N,N'-bis(diphenylphosphino)-N,N'-bis(1-phenylethyl)ethylenediamine, 1,2-bis(diphenylphosphino)propane, 2,4-bis(diphenylphosphino)pentane, cyclohexylanisylmethylphosphine, 2,3-bis(diphenylphosphino)-5-norbornene, 3,4-bis(diphenylphosphino)-1-benzylpyrrolidine, 1-[1',2-bis(diphenylphosphino)ferrocenyl]ethyl alcohol, 2,2'-bis(diphenylphosphino)-1,1'-dicyclopentane, 2,2'-bis(diphenylphosphino)-1,1-binaphthyl-5,5'-disulfonic acid sodium salt, 2,2'-bis(di(3,5-xylyl)phosphino)-1,1-binaphthyl-5,5'-disulfonic acid sodium salt, 1,1-(2,2'-bis(diphenylphosphino)-1,1'-binaphthyl-6,6'-diyl)bis(methylene)guanidine, 1,1-(2,2'-bis(di(3,5-xylyl)phosphino)-1,1'-binaphthyl-6,6'-diyl)bis(methylene)

guanidine, (6,6'-bis(tris(3,3,4,4,5,5,6,6,7,7,8,8,8-tridecafluorooctyl)silyl)-1,1'-binaphthyl-2,2'-diyl)bis(diphenylphosphine), (6,6'-bis(tris(3,3,4,4,5,5,6,6,7,7,8,8,8-tridecafluorooctyl)silyl)-1,1'-binaphthyl-2,2'-diyl)bis(di(3,5-xylyl)phosphine), (2,2'-bis(diphenylphosphino)-1,1'-binaphthyl-4,4'-diyl)dimethanamine hydrobromide, (2,2'-bis(di(3,5-xylyl)phosphino)-1,1'-binaphthyl-4,4'-diyl)dimethanamine hydrobromide, (4,4'-bis(trimethylsilyl)-1,1'-binaphthyl-2,2'-diyl)bis(diphenylphosphine), (4,4'-bis(trimethylsilyl)-1,1'-binaphthyl-2,2'-diyl)bis(di(3,5-xylyl)phosphine), (4,4'-bis(triisopropylsilyl)-1,1'-binaphthyl-2,2'-diyl)bis(diphenylphosphine), (4,4'-bis(triisopropylsilyl)-1,1'-binaphthyl-2,2'-diyl)bis(di(3,5-xylyl)phosphine), 2,2'-bis(diphenylphosphino)-1,1'-binaphthyl-4,4'-diyldiphosphonic acid, 2,2'-bis(di(3,5-xylyl)phosphino)-1,1'-binaphthyl-4,4'-diyldiphosphonic acid, tetraethyl 2,2'-bis(diphenylphosphino)-1,1'-binaphthyl-4,4'-diyldiphosphonate, tetraethyl 2,2'-bis(di(3,5-xylyl)phosphino)-1,1'-binaphthyl-4,4'-diyldiphosphonate, (4,4'-diphenyl-1,1'-binaphthyl-2,2'-diyl)bis(diphenylphosphine), (4,4'-diphenyl-1,1'-binaphthyl-2,2'-diyl)bis(di(3,5-xylyl)phosphine), (4,4'-dichloro-1,1'-binaphthyl-2,2'-diyl)bis(diphenylphosphine), (4,4'-dichloro-1,1'-binaphthyl-2,2'-diyl)bis(di(3,5-xylyl)phosphine), (4,4'-dibromo-1,1'-binaphthyl-2,2'-diyl)bis(diphenylphosphine), (4,4'-dibromo-1,1'-binaphthyl-2,2'-diyl)bis(di(3,5-xylyl)phosphine), (4,4'-dimethyl-1,1'-binaphthyl-2,2'-diyl)bis(diphenylphosphine), (4,4'-dimethyl-1,1'-binaphthyl-2,2'-diyl)bis(di(3,5-xylyl)phosphine), (2,2'-bis(diphenylphosphino)-1,1'-binaphthyl-4,4'-diyl)bis(diphenylmethanol), (2,2'-bis(di(3,5-xylyl)phosphino)-1,1'-binaphthyl-4,4'-diyl)bis(diphenylmethanol), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(diphenylphosphine), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(di(3,5-xylyl)phosphine), (7,7'-dimethoxy-1,1'-binaphthyl-2,2'-diyl)bis(diphenylphosphine), (7,7'-dimethoxy-1,1'-binaphthyl-2,2'-diyl)bis(di(3,5-xylyl)phosphine), 4,4'-di-tert-butyl-4,4',5,5'-tetrahydro-3H,3'H-3,3'-bidinaphtho[2,1-c:1',2'-e]phosphepine, 1,2-bis(3H-dinaphtho[2,1-c:1',2'-e]phosphepin-4(5H)-yl)benzene, 3,3'-bis(diphenylphosphino)-4,4'-biphenanthrene, 3,3'-bis(di(3,5-xylyl)phosphino)-4,4'-biphenanthrene, (3,3'-diphenyl-1,1'-binaphthyl-2,2'-diyl)bis(methylene)bis(diphenylphosphine), (3,3'-diphenyl-1,1'-binaphthyl-2,2'-diyl)bis(methylene)bis(di(3,5-xylyl)phosphine), 2,2'-bis(diphenylphosphinoxy)-1,1'-binaphthyl, 2,2'-bis(di(3,5-xylyl)phosphinoxy)-1,1'-binaphthyl, (3,3'-dimethyl-1,1'-binaphthyl-2,2'-diyl)bis(oxy)bis(diphenylphosphine), (3,3'-dimethyl-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(diphenylphosphine), (3,3'-diphenyl-1,1'-binaphthyl-2,2'-diyl)bis(oxy)bis(di(3,5-xylyl)phosphine), (3,3'-bis(3,5-dimethylphenyl)-1,1'-binaphthyl-2,2'-diyl)bis(oxy)bis(diphenylphosphine), (3,3'-bis(3,5-dimethylphenyl)-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(bis(3,5-dimethylphenyl)phosphine), N2,N2'-bis(diphenylphosphino)-1,1'-binaphthyl-2,2'-diamine, N2,N2'-bis(di(3,5-xylyl)phosphino)-1,1'-binaphthyl-2,2'-diamine, (Sp)-1-[(S)-α-(dimethylamino)-2-(diphenylphosphino)benzyl]-2-diphenylphosphinoferrocene, (Rp)-1-[(R)-α-(dimethylamino)-2-(diphenylphosphino)benzyl]-2-diphenylphosphinoferrocene, (R)-1-{(Rp)-2-[2-(diphenylphosphino)phenyl]ferrocenyl}ethyldicyclohexylphosphine, (S)-1-{(Sp)-2-[2-(diphenylphosphino)phenyl]ferrocenyl}ethyldicyclohexylphosphine, (R)-1-{(Rp)-2-[2-(diphenylphosphino)phenyl]ferrocenyl}ethyldicyclohexylphosphine, (S)-1-{(Sp)-2-[2-(diphenylphosphino)phenyl]ferrocenyl}ethyldicyclohexylphosphine, (R)-1-{(Rp)-2-[2-(diphenylphosphino)phenyl]ferrocenyl}ethyldi(2-norbonyl)phosphine, (S)-1-{(Sp)-2-[2-(diphenylphosphino)phenyl]ferrocenyl}ethyldi(2-norbonyl)phosphine, (R)-1-{(Rp)-2-[2-(diphenylphosphino)phenyl]ferrocenyl}ethyldi(3,5-xylyl)phosphine, (S)-1-{(Sp)-2-[2-(diphenylphosphino)phenyl]ferrocenyl}ethyldi(3,5-xylyl)phosphine, (R)-1-{(Rp)-2-[2-[di(3,5-xylyl)phosphino]phenyl]ferrocenyl}ethyldi(3,5-xylyl)phosphine, (S)-1-{(Sp)-2-[2-[di(3,5-xylyl)phosphino]phenyl]ferrocenyl}ethyldi(3,5-xylyl)phosphine, (R)-1-{(Rp)-2-[2-(diphenylphosphino)phenyl]ferrocenyl}ethylbis[3,5-bis-(trifluoromethyl)phenyl]phosphine, (S)-1-{(Sp)-2-[2-(diphenylphosphino)phenyl]ferrocenyl}ethylbis[3,5-bis-(trifluoromethyl)phenyl]phosphine, (R)-1-{(Rp)-2-[2-[bis(4-methoxy-3,5-dimethylphenyl)phosphino]phenyl]ferrocenyl}ethylbis[3,5-bis(trifluoromethyl)phenyl]phosphine, (S)-1-{(Sp)-2-[2-[bis(4-methoxy-3,5-dimethylphenyl)phosphino]phenyl]ferrocenyl}ethylbis[3,5-bis(trifluoromethyl)phenyl]phosphine, 3,3',4,4'-tetramethyl-1,1'-diphenyl-2,2',5,5'-tetrahydro-1H,1'H-2,2'-biphosphole, 1,1'-di-tert-butyl-2,2'-biphospholane, 2,2'-di-tert-butyl-2,2',3,3'-tetrahydro-1H,1'H-1,1'-bisisophosphindole, 1,2-bis(2,4-dimethylphosphetan-1-yl)ethane, 1,2-bis(2,5-dimethylpholan-1-yl)ethane, 1,2-bis(2,4-dimethylphosphetan-1-yl)benzene, 1,2-bis(2,5-dimethylpholan-1-yl)benzene, 3,4-bis(2,5-dimethylpholan-1-yl)furan-2,5-dione, 3,4-bis(2,5-diethylpholan-1-yl)furan-2,5-dione, 3,4-bis(2,5-dimethylpholan-1-yl)-1-phenyl-1H-pyrrole-2,5-dione, 1-(3,5-bis(trifluoromethyl)phenyl)-3,4-bis(2,5-dimethylpholan-1-yl)-1H-pyrrole-2,5-dione, 1-((1R,2S,4R,5S)-2,5-dimethyl-7-phosphabicyclo[2.2.1]heptan-7-yl)-2-((2R,5S)-2,5-dimethyl-7-phosphabicyclo[2.2.1]heptan-7-yl)benzene, 1,1'-(benzo[b]thiophene-2,3-diyl)bis(2,5-dimethylpholane), (2,2',4,4'-tetramethyl-3,3',4,4'-tetrahydro-2H,2'H-6,6'-bibenzo[b][1,4]dioxepin-7,7'-diyl)bis(diphenylphosphine), (2,2',4,4'-tetramethyl-3,3',4,4'-tetrahydro-2H,2'H-6,6'-bibenzo[b][1,4]dioxepin-7,7'-diyl)bis(di(3,5-xylyl)phosphine), ((6R)-6,7-dimethyl-6,7-dihydrodibenzo[e,g][1,4]dioxocin-1,12-diyl)bis(diphenylphosphine), ((6R)-6,7-dimethyl-6,7-dihydrodibenzo[e,g][1,4]dioxocin-1,12-diyl)bis(di(3,5-xylyl)phosphine), (4,4',5,5',6,6'-hexamethylbiphenyl-2,2'-diyl)bis(diphenylphosphine), (4,4',5,5',6,6'-hexamethylbiphenyl-2,2'-diyl)bis(di(3,5-xylyl)phosphine), (4,4',5,5',6,6'-hexamethoxybiphenyl-2,2'-diyl)bis(diphenylphosphine), (4,4',5,5',6,6'-hexamethoxybiphenyl-2,2'-diyl)bis(di(3,5-xylyl)phosphine), (5,5'-dichloro-4,4',6,6'-tetramethylbiphenyl-2,2'-diyl)bis(diphenylphosphine), (5,5'-dichloro-4,4',6,6'-tetramethylbiphenyl-2,2'-diyl)bis(di(3,5-xylyl)phosphine), (5,5'-dimethoxy-4,4',6,6'-tetramethylbiphenyl-2,2'-diyl)bis(diphenylphosphine), (5,5'-dimethoxy-4,4',6,6'-tetramethylbiphenyl-2,2'-diyl)bis(di(3,5-xylyl)phosphine), 2,2'-bis(diphenylphosphino)-6,6'-dimethoxybiphenyl-3,3'-diol, 2,2'-bis(di(3,5-xylyl)phosphino)-6,6'-dimethoxybiphenyl-3,3'-diol, (3,3',6,6'-tetramethoxybiphenyl-2,2'-diyl)bis(diphenylphosphine), (3,3',6,6'-tetramethoxybiphenyl-2,2'-diyl)bis(di(3,5-xylyl)phosphine), (3,3'-diisopropyl-6,6'-dimethoxybiphenyl-2,2'-diyl)bis(diphenylphosphine), (3,3'-diisopropyl-6,6'-dimethoxybiphenyl-2,2'-diyl)bis(di(3,5-xylyl)phosphine), (6,6'-dimethoxy-3,3'-bis(p-tolyloxy)biphenyl-2,2'-diyl)bis (diphenylphosphine), (6,6'-dimethoxy-3,3'-bis(p-tolyloxy) biphenyl-2,2'-diyl)bis(di(3,5-xylyl)phosphine), 2,2'-bis (diphenylphosphino)-6,6'-dimethoxybiphenyl-3,3'-diylbis (2,2-dimethyl propanoate), 2,2'-bis(di(3,5-xylyl)phosphino)-6,6'-dimethoxybiphenyl-3,3'-diylbis(2,2-dimethyl propanoate), (5,5'-dichloro-6,6'-dimethoxybiphenyl-2,2'-diyl)bis(diphenylphosphine), (5,5'-dichloro-6,6'-dimethoxy-biphenyl-2,2'-diyl)bis(di(3,5-xylyl)phosphine), 6,6'-bis (diphenylphosphino)biphenyl-2,2'-diyl diacetate, 6,6'-bis(di (3,5-xylyl)phosphino)biphenyl-2,2'-diyl diacetate, 6,6'-bis (diphenylphosphino)biphenyl-2,2'-diylbis(2,2-dimethyl propanoate), 6,6'-bis(di(3,5-xylyl)phosphino)biphenyl-2,2'-diylbis(2,2-dimethyl propanoate), 6,6'-bis(diphenylphosphino)biphenyl-2,2'-diylbis(2-methyl propanoate), 6,6'-bis (di(3,5-xylyl)phosphino)biphenyl-2,2'-diylbis(2-methyl propanoate, 6,6'-bis(diphenylphosphino)biphenyl-2,2'-diyl dicyclohexanecarboxylate, 6,6'-bis(di(3,5-xylyl)phosphino) biphenyl-2,2'-diyl dicyclohexanecarboxylate, (4,4',6,6'-tetrakis(trifluoromethyl)biphenyl-2,2'-diyl)bis(diphenylphosphine), (4,4',6,6'-tetrakis(trifluoromethyl)biphenyl-2,2'-diyl) bis(di(3,5-xylyl)phosphine), 5-methoxy-4,6-dimethyl-4',6'-bis(trifluoromethyl)biphenyl-2,2'-diyl)bis (diphenylphosphine), (5-methoxy-4,6-dimethyl-4',6'-bis (trifluoromethyl)biphenyl-2,2'-diyl)bis(di(3,5-xylyl) phosphine), (2,2,2',2'-tetramethyl-4,4'-bibenzo[d][1,3] dioxole-5,5'-diyl)bis(diphenylphosphine), (2,2,2',2'-tetramethyl-4,4'-bibenzo[d][1,3]dioxole-5,5'-diyl)bis(di(3, 5-xylyl)phosphine), 6,6'-bis(diphenylphosphino)-2,2',3,3'-tetrahydro-7,7'-bibenzofuran, 6,6'-bis(di(3,5-xylyl) phosphino)-2,2',3,3'-tetrahydro-7,7'-bibenzofuran, (2,2,2',2'-tetrafluoro-4,4'-bibenzo[d][1,3]dioxole-5,5'-diyl)bis (diphenylphosphine), (2,2,2',2'-tetrafluoro-4,4'-bibenzo[d] [1,3]dioxole-5,5'-diyl)bis(di(3,5-xylyl)phosphine), 2-(naphthyl)-8-diphenylphosphino-1-[3,5-dioxa-4-phosphacyclohepta[2,1-a;3,4-al dinaphthalen-4-yl]-1,2-dihydroquinoline, 4,12-bis(di(3,5-xylyl)phosphino)-[2.2]-paracyclophane, 7,7'-bis(di(3,5-xylyl)phosphino)-2,2',3,3'-tetrahydro-1,1'-spirobiindane (Xyl-SDP), 7,7'-bis (diphenylphosphino)-2,2',3,3'-tetrahydro-1,1'-spirobiindane (SDP), bis(2-diphenylphosphinophenyl) ether (DPEphos), 4,5-bis(diphenylphosphinomethyl)-2,2-dimethyl-1,3-dioxolane (DIOP), 1,2-bis(diphenylphosphino)propane (PROPHOS), 2,3-bis(diphenylphosphino)butane (CHIRAPHOS), 1,2-bis[(2-methoxyphenyl)(phenyl)phosphino]ethane (DIPAMP), 3,4-bis(diphenylphosphino)-1-benzylpyrrolidine (DEGUPHOS), 2,3-bis(diphenylphosphino)-bicyclo[2.2.1] hept-5-ene (NORPHOS), 1-tertiarybutoxycarbonyl-4-diphenylphosphino-2-(diphenylphosphinomethyl)pyrrolidine (BPPM), (2,2'-bis-(dibenzofuran-3,3-diyl)-bis-diphenylphosphine (BIBFUP), 2,2-bis(diphenylphosphino)-3,3-binaphtho[b]furan (BINAPFu), 2,2'-bis(diphenylphosphino)-3,3'-bi[benzo[b]thiophene] (BITIANP), N,N-dimethyl-7,7'-bis(di(3,5-xylyl)phosphino)-3,3',4,4'-tetrahydro-8,8'-bi-2H-1,4-benzoxazine (Xyl-Solphos), 2,3-bis(tertiary-butylmethylphosphino)quinoxaline (QuinoxP*), 2,4-bis(diphenylphosphino)pentane (SKEWPHOS), 2,4-bis (di(3,5-xylyl)phosphino)pentane (XylSKEWPHOS), 4,4'-bis(diphenylphosphino)-2,2',5,5'-tetramethyl-3,3'-bithiophene (TMBTP), 3,3'-bis(diphenylphosphonyl)-1,1'-2, 2'-biindole (N-Me-2-BINPO), (2,2',5,5'-tetramethyl-3,3'-bithiophene-4,4'-diyl)bis(diphenylphosphine) (BITIANP), (4,4',6,6'-tetramethyl-3,3'-bibenzo[b]thiophene-2,2'-diyl)bis (diphenylphosphine) (tetraMe-BITIANP), 1,1'-bis(diphenylphosphino)-3,3'-dimethyl-1H,1'H-2,2'-biindole (BISCAP), 2,2'-bis(diphenylphosphino)-3,3'-bibenzofuran (BICUMP), 2,2'-bis(diphenylphosphino)-1,1'-bibenzo[d] imidazole (BIMIP), and the like.

Of the optically active bisphosphine compounds described above, preferred are BINAP, TolBINAP, XylBINAP, H8-BINAP, Xyl-H8-BINAP, SEGPHOS, DM-SEGPHOS, DTBM-SEGPHOS, DMM-SEGPHOS, P-Phos, Xyl-P-Phos, Xyl-C3-TunePhos, PHANEPHOS, Xyl-PHANPHOS, Xyl-SYNPHOS, BIPHEP, MeO-BIPHEP, Xyl-MeO-BIPHEP, and the like, and more preferred are SEGPHOS, DM-SEGPHOS, DMM-SEGPHOS, MeO-BIPHEP, Xyl-MeO-BIPHEP, SYNPHOS, and the like.

The ruthenium complexes represented by general formulae (1) to (4) used for the present invention can be produced according to the methods described in Japanese Patent Application Publication No. 2011-246435, J. Am. Chem. Soc. 2011, vol. 133, p. 10696, WO2012/137460, and the like. Specifically, the ruthenium complexes represented by general formulae (1) and (3) can be produced by reacting a ruthenium compound represented by general formula (A) with a diamine compound in the presence of a base, especially an organic base. The ruthenium complexes of the present invention can also be produced by reacting a ruthenium compound represented by general formula (B) with an optically active diphosphine compound represented by ⌒P, followed by a reaction with a diamine compound in the presence of a base, especially an organic base.

[RuX'(L)(⌒P)]X' (A), wherein Ru represents a ruthenium atom, X' represents an anionic group, L represents an arene, and ⌒P represents an optically active diphosphine.

[Ru(X')$_2$(L)]$_m$ (B), wherein Ru represents a ruthenium atom, X' represents an anionic group, L represents an arene, and m represents a natural number of 2 or larger.

The ruthenium compound represented by general formula (B) (hereinafter, also referred to as an arene complex) may be commercially available one or can be produced according to an already reported method. Meanwhile, the ruthenium compound represented by general formula (A) (hereinafter, also referred to as an arene-phosphine complex) may be commercially available one or can be produced by reacting an optically active diphosphine compound represented by ⌒P with an arene complex represented by general formula (B) according to an already reported method.

The arene represented by L in each of general formulae (A) and (B) may be an optionally substituted aromatic compound which can be coordinated to a ruthenium atom and which has 6 to 20 carbon atoms, and is preferably a carbocyclic aromatic compound. Preferred arenes include benzene; o-, m-, or p-xylene; o-, m-, or p-cymene; trimethylbenzenes such as mesitylene; and the like. preferred examples of the ruthenium compound represented by general formula (B) include ruthenium compounds to which an aromatic compound is coordinated, such as [RuCl$_2$(benzene)]$_2$, [RuCl$_2$(p-cymene)]$_2$, and [RuCl$_2$(mesitylene)]$_2$. Meanwhile, preferred examples of the ruthenium compound represented by general formula (A) include ruthenium compounds in which an aromatic compound is coordinated, such as [RuCl(benzene) (⌒P)]Cl, [RuCl(p-cymene) (⌒P)]Cl, and [RuCl(mesitylene) (⌒P)]Cl.

The diamine compound may be a diamine compound in which two amino groups are present at its terminals and an aryl group is present as a substituent at the α-position of at least one of the amino groups, and preferred diamine compounds include diamine compounds represented by the following general formula (9):

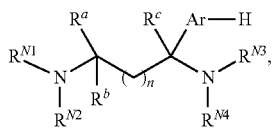

(9)

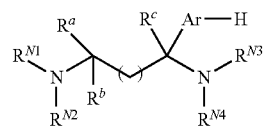

(10)

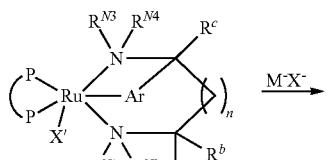

wherein $R^a$, $R^b$, and $R^c$ each independently represent a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; $R^{N1}$ and $R^a$ may together form an optionally substituted alkylene group; n represents an integer of 0 to 3; and Ar represents an optionally substituted arylene group.

Specific examples of the diamine compound represented by general formula (9) and used in the present invention include 1,2-diphenylethylenediamine, 1,2-bis(4-methoxyphenyl)ethylenediamine, 1-methyl-2,2-diphenylethylenediamine, 1-isobutyl-2,2-diphenylethylenediamine, 1-isopropyl-2,2-diphenylethylenediamine (DPIPEN), 1-methyl-2,2-bis(4-methoxyphenyl)ethylenediamine (DAMEN), 1-isobutyl-2,2-bis(4-methoxyphenyl)ethylenediamine, 1-isopropyl-2,2-bis(4-methoxyphenyl)ethylenediamine (DAIPEN), 1-phenyl-2,2-bis(4-methoxyphenyl)ethylenediamine, 1,1-bis(4-methoxyphenyl)ethylenediamine (DAEN), 1-isopropyl-2,2-bis(3-methoxyphenyl)ethylenediamine (3-DAIPEN), 1-isopropyl-2,2-bis(4-fluorophenyl)ethylenediamine (F-DAIPEN), and the like. The above-described diamine compounds may be optically active diamine compounds. When the diamine compound is optically active, a prefix such as (R) or (S) which indicates that the compound is optically active is added before the name of the compound.

Of the above-described diamine compounds, preferred are DPIPEN, DAIPEN, DAMEN, DAEN, 3-DAIPEN, F-DAIPEN, and the like, and more preferred are DAIPEN, F-DAIPEN, DPIPEN, and the like.

The ruthenium complexes of general formulae (2) and (4) used in the present invention can be produced by reacting the ruthenium compound represented by general formula (A) with the diamine compound, followed by reaction with a metal salt, according to the following reaction formula (10). In addition, the ruthenium complex of the present invention can be produced according to the following reaction formula (11) as follows. Specifically, the ruthenium compound represented by general formula (B) is reacted with the diphosphine compound represented by ⌒P, then reacted with the diamine compound, and then reacted with a metal salt. It is possible to produce the ruthenium complex either by isolating the complex of general formula (1), followed by a reaction with a metal salt, or by reacting the complex of general formula (1) with a metal salt without isolation. The ruthenium complex is preferably produced by isolating the complex of general formula (1), followed by reaction with the metal salt.

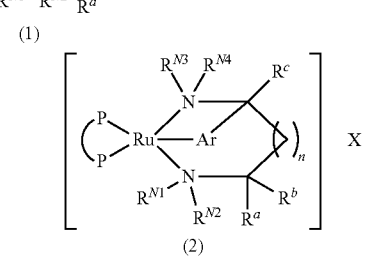

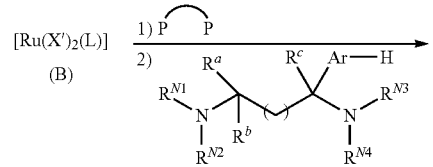

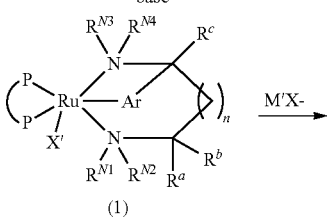

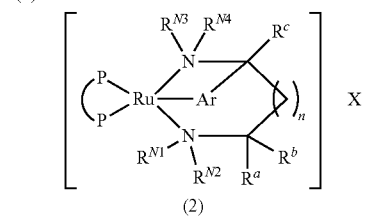

As the ruthenium complexes of general formulae (1) to (4) used in the present invention, commercially available ones may be used, or self-prepared ones may be used. When the ruthenium complex is used as a catalyst, the complex whose purity has been increased by a method such as concentration, vacuum concentration, solvent extraction, washing, recrystallization, or silica gel column chromatography after the reaction for synthesizing the ruthenium complex may be used, or the complex may be used without purification.

The use of any one of the ruthenium complexes shown in general formulae (1) to (4) as an asymmetric hydrogenation catalyst makes it possible to produce an optically active amine by an asymmetric hydrogenation of a prochiral carbon-nitrogen double bond. The production method of the present invention is particularly excellent in terms of enantioselectivity and the like, and is suitable as a method for producing an optically active amine compound from a compound having a prochiral carbon-nitrogen double bond, for example, a prochiral imine.

The asymmetric hydrogenation is described below.

The asymmetric hydrogenation reaction of a prochiral carbon-nitrogen double bond of the present invention may be a reaction represented by formula (12) in which an optically active amine (D) is produced by asymmetric hydrogenation of an imine compound (C):

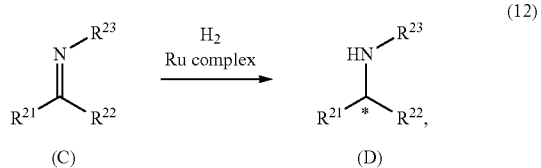

(12)

(C)    (D)

wherein $R^{21}$ and $R^{22}$ are different from each other and each represent an optionally substituted alkyl group, an optionally substituted (hetero)aryl group, or an optionally substituted aralkyl group, $R^{23}$ represents a hydrogen atom, an optionally substituted alkyl group, an optionally substituted aryl group, or an optionally substituted aralkyl group, or $R^{21}$ and $R^{22}$, $R^{21}$ and $R^{23}$, or $R^{22}$ and $R^{23}$ may form an asymmetric cyclic imine; and * indicates an asymmetric carbon.

The alkyl group represented by $R^{21}$, $R^{22}$, or $R^{23}$ in the above-described compounds (C) and (D) is, for example, an alkyl group having 1 to 8 carbon atoms. The (hetero)aryl group represented by $R^{21}$, $R^{22}$, or $R^{23}$ may be phenyl, naphthyl, pyridyl, pyrimidinyl, furyl, thienyl, or the like, and the substituents thereof include alkyl groups having 1 to 6 carbon atoms, alkoxy groups having 1 to 6 carbon atoms, halogen atoms, and the like. The alkyl in the aralkyl group may be an alkyl group having 1 to 12 carbon atoms, and the substituents thereof include alkyl groups having 1 to 6 carbon atoms, alkoxy groups having 1 to 6 carbon atoms, halogen atoms, and the like. Typical imine substrates of this type include N-(1-phenylethylidene)aniline, N-(1-phenylethylidene)benzylamine, and the like.

Examples of the imine in which $R^{21}$ and $R^{22}$, $R^{21}$ and $R^{23}$, or $R^{22}$ and $R^{23}$ forms a ring include compounds having N-2,3-dihydro-1H-indan-2-ylidene, 2H-pyrrole, 3,4-dihydro-2H-pyrrole, oxazole, benzoxazole, benzothiazole, isoxazole, triazole, isothiazole, 2,3,4,5-tetrahydropyridine, 3H-indole, 3,4-dihydroquinoline, 3,4-dihydroisoquinoline, quinoxaline, oxazine, 2H-1,4-benzoxazine, 2H-1,4-benzothiazine, pyridine, quinoline, isoquinoline, indole, isoindole, 1H-indazole, imidazole, 2H-imidazole, benzimidazole, phthalazine, quinazoline, 2-imidazoline, pyrazole, triazole, furazan, tetrazole, triazine, pyrimidine, triazine, acridine, phenanthridine, phenanthroline, phenazine, naphthyridine, purine, or pteridin, and the like. Each of these compounds may have a substituent(s). The substituents include alkyl groups having 1 to 6 carbon atoms, alkoxy groups having 1 to 6 carbon atoms, halogen atoms, aryl groups, and the like. More preferred imines include quinoxaline derivatives, 2H-1,4-benzoxazine derivatives, and the like.

The asymmetric hydrogenation reaction of a quinoxaline derivative may be a reaction represented by formula (13) in which an optically active amine (F) is produced by an asymmetric hydrogenation of a quinoxaline derivative (E):

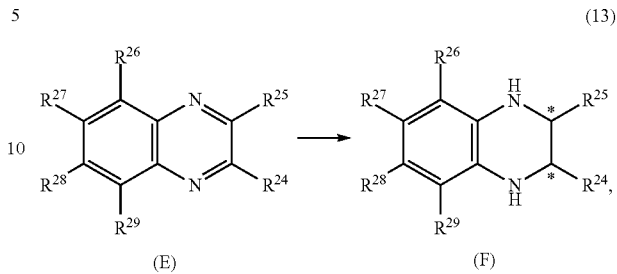

(13)

(E)    (F)

wherein $R^{24}$, $R^{25}$, $R^{26}$, $R^{27}$, $R^{28}$, and $R^{29}$ each independently represent a hydrogen atom, a halogen atom, an optionally substituted alkyl group, an optionally substituted (hetero)aryl group, an optionally substituted $C_3$ to $C_8$ cycloalkyl group, a tri-substituted silyl group, an optionally substituted alkoxy group, or an optionally substituted aralkyl group, provided that one of $R^{24}$ and $R^{25}$ is not a hydrogen atom; and * indicates an asymmetric carbon.

The halogen atom represented by each of $R^{24}$, $R^{25}$, $R^{26}$, $R^{27}$, $R^{28}$, and $R^{29}$ in the above-described compounds (E) and (F) may be a chlorine atom, a bromine atom, an iodine atom, a fluorine atom, or the like. Examples of the alkyl group include alkyl groups having 1 to 8 carbon atoms, and the substituents thereof include alkoxy groups having 1 to 6 carbon atoms, halogen atoms, and the like. The (hetero)aryl group may be phenyl, naphthyl, pyridyl, pyrimidinyl, furyl, thienyl, or the like, and substituents thereof include alkyl groups having 1 to 6 carbon atoms, alkoxy groups having 1 to 6 carbon atoms, halogen atoms, and the like. The $C_3$ to $C_8$ cycloalkyl group may be a cyclopropyl group, a cyclopentyl group, a cyclohexyl group, or the like, and the substituents thereof include alkyl groups having 1 to 6 carbon atoms, alkoxy groups having 1 to 6 carbon atoms, halogen atoms, and the like. The tri-substituted silyl group may be a silyl group tri-substituted by the above-described alkyl groups or aryl groups, and examples thereof include a trimethylsilyl group, a triethylsilyl group, a triisopropylsilyl group, a t-butyldimethylsilyl group, a diphenylmethylsilyl group, a dimethylphenylsilyl group, and the like. The alkoxy group may be a methoxy group, an ethoxy group, a n-propoxy group, an isopropoxy group, a n-butoxy group, a s-butoxy group, an isobutoxy group, a t-butoxy group, or the like, and the substituents thereof include alkyl groups having 1 to 6 carbon atoms, alkoxy groups having 1 to 6 carbon atoms, halogen atoms, and the like. The alkyl in the aralkyl group may be an alkyl group having 1 to 12 carbon atoms, and the substituents thereof include alkyl groups having 1 to 6 carbon atoms, alkoxy groups having 1 to 6 carbon atoms, halogen atoms, and the like.

The asymmetric hydrogenation reaction of a 2H-1,4-benzoxazine or 2H-1,4-benzothiazine derivative may be a reaction represented by formula (14) in which an optically active amine (H) is produced by an asymmetric hydrogenation of a 2H-1,4-benzoxazine derivative (Y: oxygen atom) or a 2H-1,4-benzothiazine derivative (Y: sulfur atom) (G):

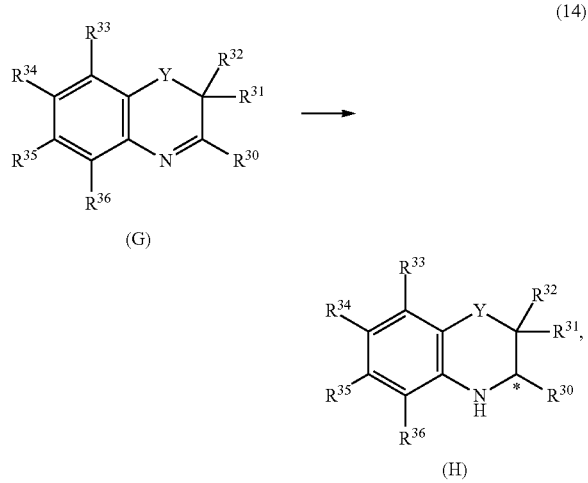

wherein Y represents an oxygen atom or a sulfur atom, $R^{30}$, $R^{31}$, $R^{32}$, $R^{33}$, $R^{34}$, $R^{35}$, and $R^{36}$ each independently represent a hydrogen atom, a halogen atom, an optionally substituted alkyl group, an optionally substituted (hetero)aryl group, an optionally substituted $C_3$ to $C_8$ cycloalkyl group, a tri-substituted silyl group, an optionally substituted alkoxy group, or an optionally substituted aralkyl group; * indicates an asymmetric carbon; and when $R^{31}$ and $R^{32}$ are the same substituents, the carbon atom to which $R^{31}$ and $R^{32}$ are bound is not an asymmetric carbon.

The halogen atom represented by each of $R^{30}$, $R^{31}$, $R^{32}$, $R^{33}$, $R^{34}$, $R^{35}$, and $R^{36}$ in the above-described compounds (G) and (H) may be a chlorine atom, a bromine atom, an iodine atom, a fluorine atom, or the like. The alkyl group is, for example, an alkyl group having 1 to 8 carbon atoms, and the substituents thereof include alkoxy groups having 1 to 6 carbon atoms, halogen atoms, and the like. The (hetero)aryl group may be a phenyl group, a naphthyl group, a pyridyl group, a pyrimidinyl group, a furyl group, a thienyl group, or the like, and the substituents thereof include alkyl groups having 1 to 6 carbon atoms, alkoxy groups having 1 to 6 carbon atoms, halogen atoms, and the like. The $C_3$ to $C_8$ cycloalkyl group may be a cyclopropyl group, a cyclopentyl group, a cyclohexyl group, or the like, and the substituents thereof include alkyl groups having 1 to 6 carbon atoms, alkoxy groups having 1 to 6 carbon atoms, halogen atoms, and the like. The tri-substituted silyl group may be a silyl group tri-substituted by the above-described alkyl groups or aryl groups, and examples thereof include a trimethylsilyl group, a triethylsilyl group, a triisopropylsilyl group, a tert-butyldimethylsilyl group, a diphenylmethylsilyl group, a dimethylphenylsilyl group, and the like. The alkoxy group may be a methoxy group, an ethoxy group, a n-propoxy group, an isopropoxy group, a n-butoxy group, a s-butoxy group, an isobutoxy group, a t-butoxy group, or the like, and the substituents thereof include alkyl groups having 1 to 6 carbon atoms, alkoxy groups having 1 to 6 carbon atoms, halogen atoms, and the like. The alkyl in the aralkyl group may be an alkyl group having 1 to 12 carbon atoms, and the substituents thereof include alkyl groups having 1 to 6 carbon atoms, alkoxy groups having 1 to 6 carbon atoms, halogen atoms, and the like.

The production method of the present invention can be preferably carried out without any solvent or in a solvent. It is preferable to use a solvent. The solvent used is preferably one capable of dissolving the substrate and the catalyst, and a single solvent or a mixture solvent is used. Specifically, the solvents include aromatic hydrocarbons such as toluene and xylene; aliphatic hydrocarbons such as hexane and heptane; halogenated hydrocarbons such as methylene chloride, 1,2-dichloroethane, and chlorobenzene; ethers such as diethyl ether, tetrahydrofuran, methyl t-butyl ether, and cyclopentyl methyl ether; alcohols such as methanol, ethanol, 2-propanol, n-butyl alcohol, 2-butanol, and t-butyl alcohol; polyols such as ethylene glycol, propylene glycol, 1,2-propanediol, and glycerin; acetonitrile; N,N-dimethylformamide; dimethyl sulfoxide; and the like. Of these solvents, preferred are ethers and alcohols, and particularly preferred solvents include toluene, methylene chloride, tetrahydrofuran, methanol, ethanol, 2-propanol, and t-butyl alcohol. The amount of the solvent used can be selected, as appropriate, according to the reaction conditions and the like. If necessary, the reaction is carried out with stirring.

The amount of the catalyst used varies depending on the substrate to be reduced, the reaction conditions, the kind of the catalyst, and the like. In general, the mole ratio of the ruthenium metal to the reduction substrate is in a range from 0.00001% by mole to 2% by mole, and preferably from 0.0001% by mole to 1% by mole.

In addition, the asymmetric hydrogenation of the present invention is preferably conducted by further adding a base compound. The base compound used may be an inorganic base, an organic base, or the like. The inorganic base may be potassium carbonate ($K_2CO_3$), potassium hydroxide (KOH), lithium hydroxide (LiOH), sodium hydrogen carbonate ($NaHCO_3$), sodium carbonate ($Na_2CO_3$), potassium hydrogen carbonate ($KHCO_3$), sodium hydroxide (NaOH), or the like. The organic base may be an alkali or alkaline earth metal salt such as potassium methoxide (KOMe), sodium methoxide (NaOMe), lithium methoxide (LiOMe), sodium ethoxide (NaOEt), potassium isopropoxide (KO(i-Pr)), potassium t-butoxide (KO(t-Bu)), or potassium naphthalenide ($KC_{10}H_8$), or an organic amine such as triethylamine, diethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, or N-methylmorpholine. Alternatively, the base used in the present invention may be a metal hydride such as sodium hydride or potassium hydride. Each of these bases may be used alone, or two or more thereof may be used in combination. Of these base compounds, inorganic bases, alkali or alkaline earth metal salts, and the like are preferable.

Of the bases listed above, preferred are inorganic bases such as $K_2CO_3$, KOH, LiOH, $NaHCO_3$, $Na_2CO_3$, $KHCO_3$, and NaOH and alkali or alkaline earth metal salts such as KOMe, NaOMe, LiOMe, NaOEt, KO(i-Pr), KO(t-Bu), and $KC_{10}H_8$, and more preferred are inorganic bases and such as KOH, LiOH, and NaOH and alkali or alkaline earth metal salts such as KOMe, NaOMe, LiOMe, NaOEt, KO(i-Pr), and KO(t-Bu).

The amount of the base compound used is 1 to 10000 equivalents, and preferably 10 to 5000 equivalents relative to the number of moles of the ruthenium complex, or the mole ratio of the base compound to the hydrogenation substrate is in a range from 0.00001% by mole to 100% by mole, and preferably from 0.0001% by mole to 50% by mole.

In addition, in the present invention, it is also possible to use hydrogen gas without using the above-described base, if an amine-phosphine ruthenium hydride complex is generated.

In the method of the present invention, the reaction temperature at which the asymmetric hydrogenation is carried out is −30° C. to 150° C., preferably 0° C. to 100° C., and more preferably 0° C. to 60° C. If the reaction temperature is too low, a large amount of the raw material may remain unreacted. Meanwhile, if the reaction temperature is too high, decomposition of the raw material, the catalyst, or the like may occur. Hence, such temperatures are not preferable.

Regarding the hydrogen pressure for carrying out the asymmetric hydrogenation in the present invention, the reaction sufficiently proceeds at normal pressure, because this catalyst system has an extremely high activity. The hydrogen pressure is preferably 0.1 MPa to 15 MPa, and more preferably 0.1 MPa to 10 MPa. Meanwhile, the reaction time is 1 minute to 72 hours, and preferably 30 minutes to 48 hours, in which a sufficiently high conversion of the raw material can be obtained.

After completion of the reaction, the targeted optically active amine can be obtained by one of or an appropriate combination of commonly employed purification methods such as extraction, filtration, crystallization, distillation, and various chromatographic techniques.

The method of the present invention provides a method for efficiently producing an optically active amine. To be commercially viable, the method has to achieve an optical purity of the amine (D) of 50% ee or higher. Preferably, it is important that the optical purity of the amine (D) is 80% ee or higher. If necessary, the optical purity of the obtained amine can be improved by recrystallization or by formation of a salt of the amine with a chiral or achiral acid and crystallization thereof. For commercialization of the method of the present invention, it is important that the conversion of the substrate to the product is 70% or higher, and preferably 80% or higher.

Hereinafter, the present invention is described more specifically by showing Examples. However, the present invention is not limited to Examples below.

Example 1

Asymmetric Hydrogenation of 2-Methylquinoxaline

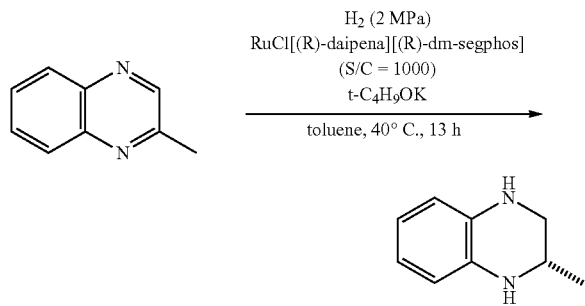

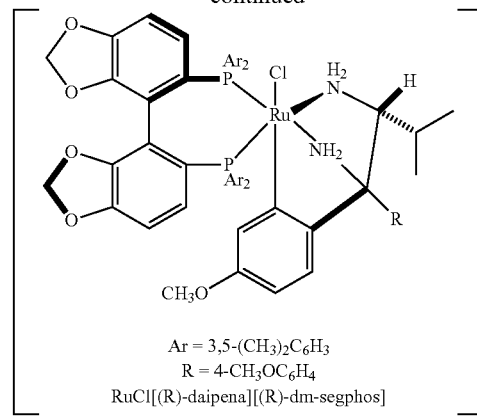

To an argon-purged pressure-resistant glass vessel (100 mL) equipped with a magnetic stir bar, RuCl[(R)-daipena][(R)-dm-segphos] (3.1 mg, 2.6 µmol) and KO(t-Bu) (14.1 mg, 0.126 mmol) were added, and the vessel was purged with argon again. To this vessel, a toluene (2.5 mL) solution containing 2-methylquinoxaline (355.4 mg, 2.47 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 13 hours. After hydrogen was released, the solution was concentrated under reduced pressure, and the residue was purified through a silica gel short path column (hexane:ethyl acetate=1:1) to obtain (S)-1,2,3,4-tetrahydro-2-methylquinoxaline (355.1 mg, 970). A result of an analysis conducted by gas chromatography (column: CHIRASIL-DEX CB) showed that the optical purity of this product was 99% ee or higher.

Examples 2 to 11 and Comparative Example 1

Reactions using 2-methylquinoxaline as a raw material were conducted by the same method as in Example 1, except that the catalyst, the mole ratio of the substrate to the catalyst, the hydrogen pressure, the reaction temperature, and the reaction time employed in Example 1 were changed as shown in Table 1. The yield of 1,2,3,4-tetrahydro-2-methylquinoxaline was measured in the same manner as in Example 1 as follows. Specifically, after the reaction, hydrogen was released, the solution was concentrated under reduced pressure, and the residue was measured by $^1$H NMR. Also, the optical purity was measured by gas chromatography (column: CHIRASIL-DEX CB) in the same manner as in Example 1. Table 1 shows the reaction results.

A comparison of Examples 2 to 11 with Comparative Example 1 showed that the catalytic activity in Comparative Example 1 was a half or less of the catalytic activities in Examples 2 to 11, and that the optical purity of the product obtained in Comparative Example 1 was also low.

TABLE 1

|  | Catalyst a) | Substrate/Catalyst (mole ratio) | Hydrogen pressure (MPa) | Solvent | Temp. (° C.) | Time (h) | Yield (%) | Optical purity (% ee) |
|---|---|---|---|---|---|---|---|---|
| Example 2 | A | 200 | 2 | 2-Propanol | 25 | 20 | 91 | 99 |
| Example 3 | A | 200 | 2 | Ethanol | 25 | 20 | 91 | >99 |
| Example 4 | A | 200 | 2 | t-Butyl alcohol | 25 | 20 | 89 | >99 |
| Example 5 | A | 200 | 2 | THF | 25 | 19 | 93 | >99 |
| Example 6 | A | 200 | 2 | Methylene chloride | 25 | 28 | 90 | >99 |
| Example 7 | A | 100 | 0.15 | Toluene | 40 | 28 | 90 | >99 |
| Example 8 | A | 8000 | 10 | Toluene | 40 | 40 | 89 | >99 |
| Example 9 | A | 2000 | 2 | Toluene | 40 | 21 | >99 | >99 |
| Example 10 | B | 1000 | 2 | Toluene | 40 | 15 | 96 | 94 |
| Example 11 | C | 200 | 2 | 2-Propanol | 25 | 22 | 89 | 95 |
| Comp. Ex. 1 | D | 200 | 2 | 2-Propanol | 25 | 19 | 35 | 93 | a)

Catalyst A Ar = 3,5'(CH$_3$)$_2$C$_6$H$_3$

R = 4-CH$_3$OC$_6$H$_4$

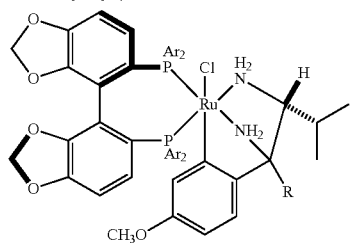

RuCl[(R)-daipena][(R)-dm-segphos]

Catalyst B Ar = C$_6$H$_5$

R = 4-CH$_3$OC$_6$H$_4$

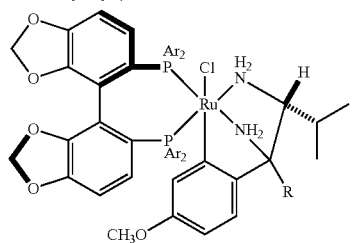

RuCl[(R)-daipena][(R)-segphos]

Catalyst C Ar = 3,5'(CH$_3$)$_2$C$_6$H$_3$

R = 4-CH$_3$OC$_6$H$_4$

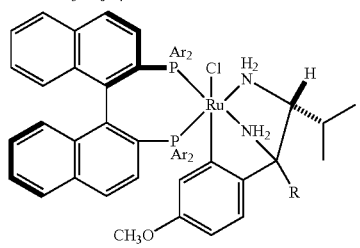

RuCl[(R)-daipena][(R)-xylbinap]

Catalyst D Ar = 3,5'(CH$_3$)$_2$C$_6$H$_3$

R = 4-CH$_3$OC$_6$H$_4$

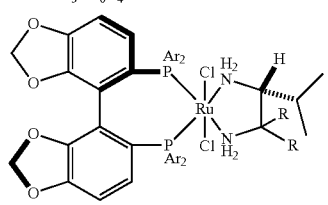

RuCl$_2$[(R)-dm-segphos][(R)-daipen]

Example 12

Asymmetric Hydrogenation of 2-Ethylquinoxaline

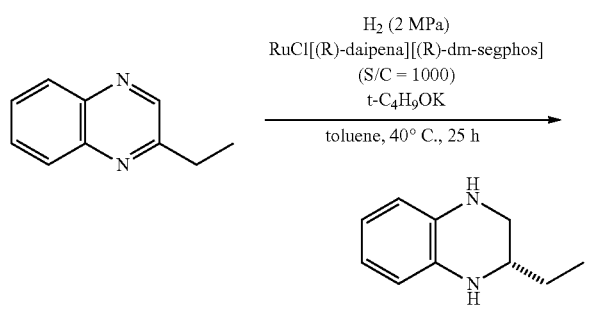

To an argon-purged pressure-resistant glass vessel (100 mL) equipped with a magnetic stir bar, RuCl[(R)-daipena][(R)-dm-segphos] (2.0 mg, 1.7 µmol) and KO(t-Bu) (9.2 mg, 0.082 mmol) were added, and the vessel was purged with argon again. To this vessel, a toluene (1.7 mL) solution containing 2-ethylquinoxaline (269.4 mg, 1.70 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 25 hours. After hydrogen was released, the solution was concentrated under reduced pressure, and the residue was purified by silica gel column chromatography (hexane:ethyl acetate=5:1 to 3:1 to 1:1) to obtain (S)-2-ethyl-1,2,3,4-tetrahydroquinoxaline (264.3 mg, 96%). A result of an analysis conducted by high performance liquid chromatography (column: CHIRALCEL OD-H, mobile phase: hexane:IPA=90:10, 1 mL/min) showed that the optical purity of this product was 99% ee or higher.

Example 13

Asymmetric Hydrogenation of 2-(1-Propyl)quinoxaline

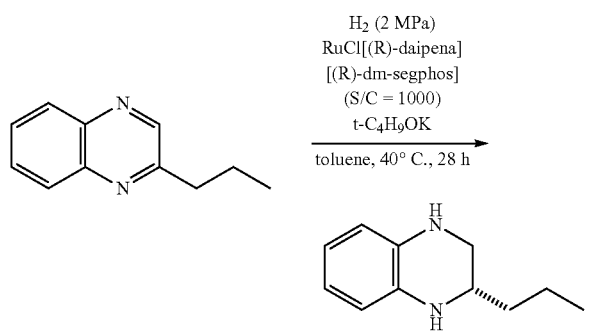

To an argon-purged pressure-resistant glass vessel (100 mL) equipped with a magnetic stir bar, RuCl[(R)-daipena][(R)-dm-segphos] (1.6 mg, 1.4 µmol) and KO(t-Bu) (8.0 mg, 0.071 mmol) were added, and the vessel was purged with argon again. To this vessel, a toluene (1.4 mL) solution containing 2-(1-propyl)quinoxaline (238.5 mg, 1.38 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 28 hours. After hydrogen was released, the solution was concentrated under reduced pressure, and the residue was purified through a silica gel short path column (ethyl acetate) to obtain (S)-1,2,3,4-tetrahydro-2-(1-propyl)quinoxaline (235.4 mg, 96%). A result of an analysis conducted by high performance liquid chromatography (column: CHIRALCEL OD-H, mobile phase: hexane:IPA=80:20, 1 mL/min) showed that the optical purity of this product was 99% ee or higher.

Example 14

Asymmetric Hydrogenation of 2-Isobutylquinoxaline

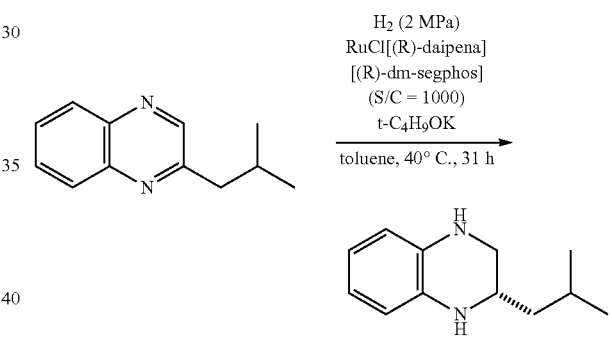

To an argon-purged pressure-resistant glass vessel (100 mL) equipped with a magnetic stir bar, RuCl[(R)-daipena][(R)-dm-segphos] (2.4 mg, 2.0 µmol) and KO(t-Bu) (11.9 mg, 0.106 mmol) were added, and the vessel was purged with argon again. To this vessel, a toluene (2.0 mL) solution containing 2-isobutylquinoxaline (378.3 mg, 2.03 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 31 hours. After hydrogen was released, the solution was concentrated under reduced pressure, and the residue was purified by silica gel column chromatography (hexane:ethyl acetate=7:1 to 4:1 to 1:1) to obtain (S)-1,2,3,4-tetrahydro-2-isobutylquinoxaline (316.4 mg, 82%). A result of an analysis was conducted by high performance liquid chromatography (column:

CHIRALCEL OD-H, mobile phase: hexane:IPA=80:20, 1 mL/min) showed that the optical purity of this product was 97% ee.

Example 15

Asymmetric Hydrogenation of 2-Benzylquinoxaline

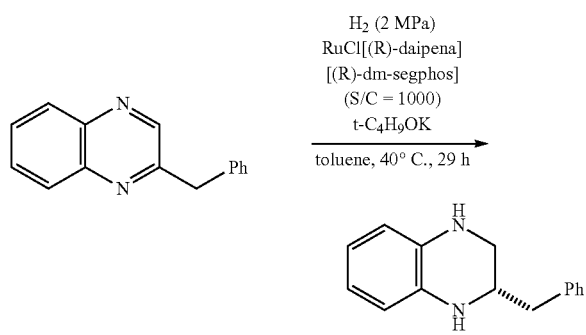

To an argon-purged pressure-resistant glass vessel (100 mL) equipped with a magnetic stir bar, RuCl[(R)-daipena][(R)-dm-segphos] (1.1 mg, 0.94 µmol) and KO(t-Bu) (5.4 mg, 0.048 mmol) were added, and the vessel was purged with argon again. To this vessel, a toluene (0.9 mL) solution containing 2-benzylquinoxaline (207.4 mg, 0.942 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 29 hours. After hydrogen was released, the solution was concentrated under reduced pressure, and the residue was purified by silica gel thin-layer chromatography (hexane:ethyl acetate=3:1) to obtain (S)-2-benzyl-1,2,3,4-tetrahydroquinoxaline (203.7 mg, 97%). A result of an analysis was conducted by high performance liquid chromatography (column: CHIRALCEL OD-H, mobile phase: hexane:IPA=90:10, 1 mL/min) showed that the optical purity of this product was 98% ee.

Example 16

Asymmetric Hydrogenation of 6-Chloro-2-methylquinoxaline

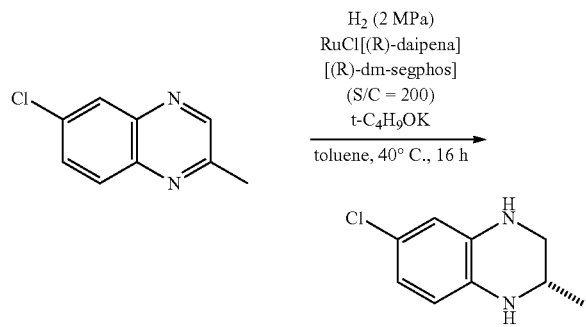

To an argon-purged pressure-resistant glass vessel (100 mL) equipped with a magnetic stir bar, RuCl[(R)-daipena][(R)-dm-segphos] (1.1 mg, 0.94 µmol) and KO(t-Bu) (5.3 mg, 0.047 mmol) were added, and the vessel was purged with argon again. To this vessel, a toluene (2.5 mL) solution containing 6-chloro-2-methylquinoxaline (33.6 mg, 0.188 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 16 hours. After hydrogen was released, the solution was concentrated under reduced pressure, and the residue was purified through a silica gel short path column (dichloromethane) to obtain (S)-6-chloro-1,2,3,4-tetrahydro-2-methylquinoxaline (33.4 mg, 97%). A result of an analysis was conducted by high performance liquid chromatography (column: CHIRALCEL OD-H, mobile phase: hexane:IPA=90:10, 1 mL/min) showed that the optical purity of this product was 99% ee or higher.

Example 17

Asymmetric Hydrogenation of 6,7-Dichloro-2-methylquinoxaline

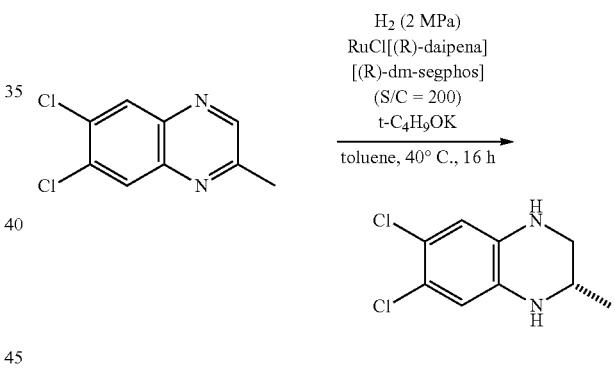

To an argon-purged pressure-resistant glass vessel (100 mL) equipped with a magnetic stir bar, RuCl[(R)-daipena][(R)-dm-segphos] (2.9 mg, 2.5 µmol) and KO(t-Bu) (14.0 mg, 0.125 mmol) were added, and the vessel was purged with argon again. To this vessel, a toluene (1.0 mL) solution containing 6,7-dichloro-2-methylquinoxaline (105.4 mg, 0.495 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 16 hours. After hydrogen was released, the solution was concentrated under reduced pressure, and the residue was purified by silica gel thin-layer chromatography (hexane:ethyl acetate=5:1) to obtain (S)-6,7-dichloro-1,2,3,4-tetrahydro-2-methylquinoxaline (102.2 mg, 95%). A result of an analysis was conducted by high performance liquid chromatography (column: CHIRALCEL OB-H, mobile phase: hexane:IPA=95:5, 1 mL/min) showed that the optical purity of this product was 98% ee.

Example 18

Asymmetric Hydrogenation of 6,7-Dichloro-2-methylquinoxaline

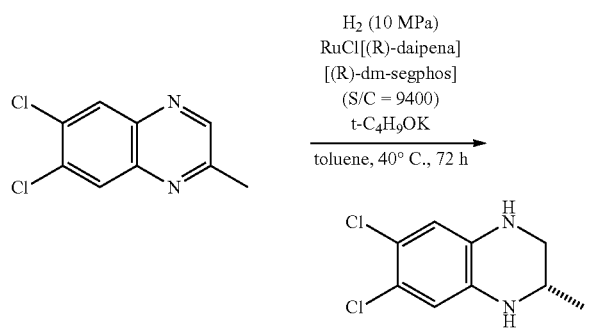

To an argon-purged pressure-resistant stainless steel vessel (50 mL) having a glass insert tube and being equipped with a magnetic stir bar, RuCl[(R)-daipena][(R)-dm-segphos] (1.0 mg, 0.85 µmol) and KO(t-Bu) (47.4 mg, 0.422 mmol) were added, and the vessel was purged with argon again. To this vessel, a toluene (4.1 mL) solution containing 6,7-dichloro-2-methylquinoxaline (1.80 g (including 5%(w/w) of 6,7-dichloro-2,3-dimethylquinoxaline, which did not participate in the reaction), 8.01 mmol (net)) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 10.0 MPa, and the vessel was stirred in a water bath at 40° C. for 72 hours. After hydrogen was released, the solution was concentrated under reduced pressure, and the residue was purified by silica gel thin-layer chromatography (dichloromethane→ethyl acetate) to obtain (S)-6,7-dichloro-1,2,3,4-tetrahydro-2-methylquinoxaline (1.69 g, 97%). A result of an analysis was conducted by high performance liquid chromatography (column: CHIRALCEL OB-H, mobile phase: hexane:IPA=95:5, 1 mL/min) showed that the optical purity of this product was 99% ee or higher.

Example 19

Asymmetric Hydrogenation of 6-Methoxy-2-methylquinoxaline

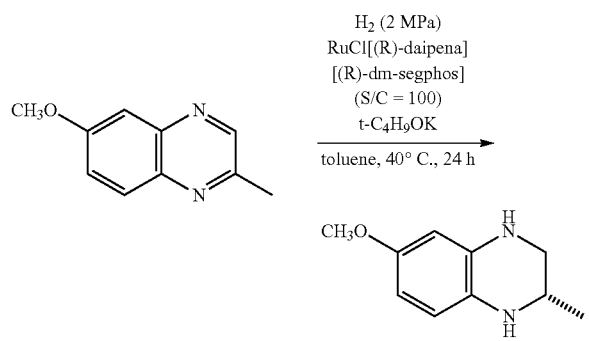

To an argon-purged pressure-resistant glass vessel (100 mL) equipped with a magnetic stir bar, RuCl[(R)-daipena][(R)-dm-segphos] (5.8 mg, 5.0 µmol) and KO(t-Bu) (15.4 mg, 0.137 mmol) were added, and the vessel was purged with argon again. To this vessel, a toluene (1.1 mL) solution containing 6-methoxy-2-methylquinoxaline (95.7 mg, 0.549 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 24 hours. After hydrogen was released, the solution was concentrated under reduced pressure, and the residue was purified through a silica gel short path column (hexane:ethyl acetate=1:1, which was subjected to nitrogen bubbling) to obtain (S)-1,2,3,4-tetrahydro-6-methoxy-2-methylquinoxaline (96.9 mg, 99%). A result of an analysis was conducted by high performance liquid chromatography (column: CHIRALCEL OD-H, mobile phase: hexane:IPA=80:20, 1 ml/min) showed that the optical purity of this product was 99% ee or higher.

Examples 20

Asymmetric Hydrogenation of 2,6,7-Trimethylquinoxaline

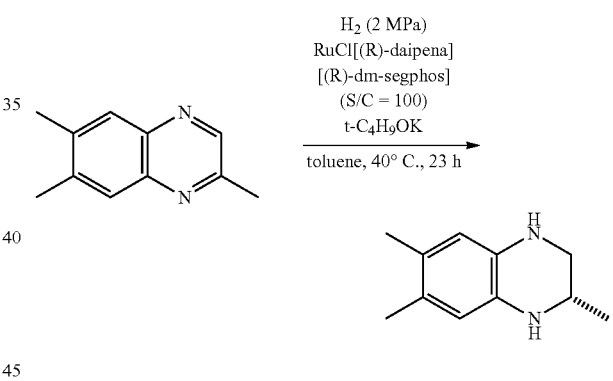

To an argon-purged pressure-resistant glass vessel (100 mL) equipped with a magnetic stir bar, RuCl[(R)-daipena][(R)-dm-segphos] (2.3 mg, 2.0 µmol) and KO(t-Bu) (10.9 mg, 0.0971 mmol) were added, and the vessel was purged with argon again. To this vessel, a toluene (0.4 mL) solution containing 2,6,7-trimethylquinoxaline (32.9 mg, 0.191 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 23 hours. After hydrogen was released, the solution was concentrated under reduced pressure, and the residue was purified through a silica gel short path column (ethyl acetate subjected to nitrogen bubbling) to obtain (S)-1,2,3,4-tetrahydro-2,6,7-trimethylquinoxaline (32.6 mg, 97%). A result of an analysis was conducted by high performance liquid chromatography (column: CHIRALCEL OD-H, mobile phase: hexane: IPA=90:10, 1 mL/min) showed that the optical purity of this product was 99% ee or higher.

Examples 21

Asymmetric Hydrogenation of 2-Phenylquinoxaline

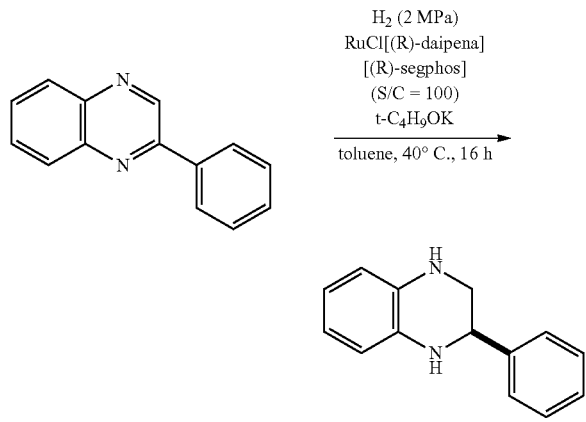

To an argon-purged pressure-resistant glass vessel (100 mL) equipped with a magnetic stir bar, RuCl[(R)-daipena][(R)-segphos] (2.0 mg, 1.9 μmol) and KO(t-Bu) (10.3 mg, 0.0918 mmol) were added, and the vessel was purged with argon again. To this vessel, a toluene (0.38 mL) solution containing 2-phenylquinoxaline (39.0 mg, 0.189 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 16 hours. After hydrogen was released, the solution was concentrated under reduced pressure, and the residue was purified by silica gel thin-layer chromatography (hexane:ethyl acetate=4:1 to 2:1) to obtain (R)-1,2,3,4-tetrahydro-2-phenylquinoxaline (39.3 mg, 99%). A result of an analysis was conducted by high performance liquid chromatography (column: CHIRALCEL OD-H, mobile phase: hexane:IPA=90:10, 1 mL/min) showed that the optical purity of this product was 96% ee.

Examples 22

Asymmetric Hydrogenation of 7,8-Difluoro-3-methyl-2H-1,4-benzoxazine

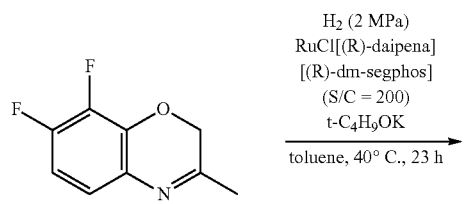

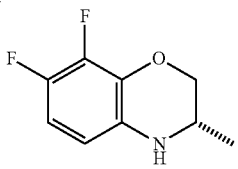

To an argon-purged pressure-resistant glass vessel (100 mL) equipped with a magnetic stir bar, RuCl[(R)-daipena][(R)-dm-segphos] (2.8 mg, 2.3 μmol) and KO(t-Bu) (13.2 mg, 0.118 mmol) were added, and the vessel was purged with argon again. To this vessel, a toluene (0.9 mL) solution containing 7,8-difluoro-3-methyl-2H-1,4-benzoxazine (84.9 mg, 0.464 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was starred in a water bath at 40° C. for 23 hours. After hydrogen was released, the solution was concentrated under reduced pressure, and the residue was purified through a silica gel short path column (hexane:ethyl acetate=1:1) to obtain (S)-7,8-difluoro-3,4-dihydro-3-methyl-2H-1,4-benzoxazine (84.1 mg, 98%). A result of an analysis was conducted by high performance liquid chromatography (column: CHIRALCEL OD-H, mobile phase: hexane:IPA=98:2, 1 mL/min) showed that the optical purity of this product was 98% ee.

Examples 23

Asymmetric Hydrogenation of 3-Phenyl-2H-1,4-benzoxazine

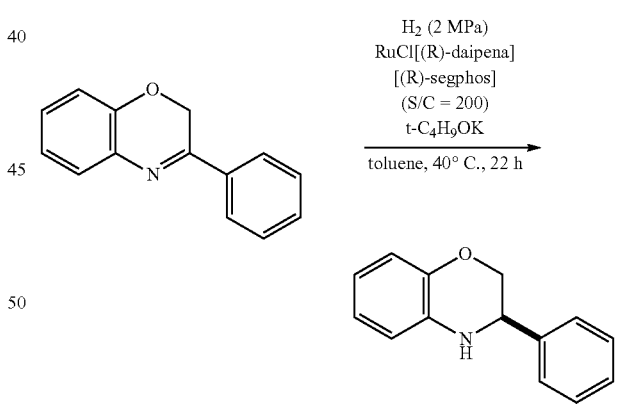

To an argon-purged pressure-resistant glass vessel (100 mL) equipped with a magnetic stir bar, RuCl[(R)-daipena][(R)-segphos] (3.3 mg, 3.1 μmol) and KO(t-Bu) (17.1 mg, 0.152 mmol) were added, and the vessel was purged with argon again. To this vessel, a toluene (1.2 mL) solution containing 3-phenyl-2H-1,4-benzoxazine (128.7 mg, 0.615 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 22 hours. After hydrogen was released, the solution was concentrated under reduced pressure, and the residue was purified through a silica gel short path column (hexane:ethyl acetate=1:1) to obtain (R)-3,4-dihydro-3-phenyl-2H-1,4-benzoxazine (130.1 mg, 990). A result of an analysis was conducted by high performance liquid chromatography (column: CHIRALCEL OD-H, mobile phase: hexane:IPA=70:30, 0.7 mL/min) showed that the optical purity of this product was 98% ee.

Examples 24

Asymmetric Hydrogenation of 3-(4-Bromophenyl)-2H-1,4-benzothiazine

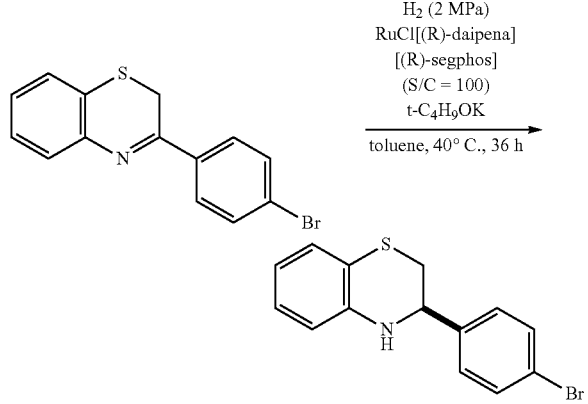

To an argon-purged pressure-resistant glass vessel (100 mL) equipped with a magnetic stir bar, RuCl[(R)-daipena][(R)-segphos] (3.3 mg, 3.1 μmol) and KO(t-Bu) (17.7 mg, 0.158 mmol) were added, and the vessel was purged with argon again. To this vessel, a toluene (0.6 mL) solution containing 3-(4-bromophenyl)-2H-1,4-benzothiazine (94.1 mg, 0.309 mmol) and being degassed by the freeze-pump-thaw technique in advance was added by pressure transfer using a cannula. An operation in which hydrogen was introduced into the pressure-resistant vessel up to 0.8 MPa and then released was repeated 10 times to completely substitute the inside with hydrogen. Then, hydrogen was introduced up to 2.0 MPa, and the vessel was stirred in a water bath at 40° C. for 36 hours. After hydrogen was released, the solution was concentrated under reduced pressure, and the residue was purified through a silica gel short path column (hexane:ethyl acetate=1:1) to obtain (R)-3-(4-bromophenyl)-1,2,3,4-tetrahydro-2H-1,4-benzothiazine (92.7 mg, 98%). A result of an analysis was conducted by high performance liquid chromatography (column: CHIRALCEL OD-H, mobile phase: hexane:IPA=80:20, 0.6 mL/min) showed that the optical purity of this product was 99% ee.

The invention claimed is:

1. A method for producing an optically active amine compound, comprising:

performing an asymmetric hydrogenation of a prochiral carbon-nitrogen double bond in the presence of a ruthenium complex of the following general formula (1) or (2):

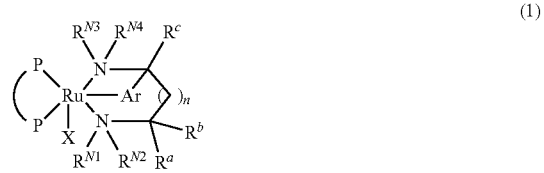

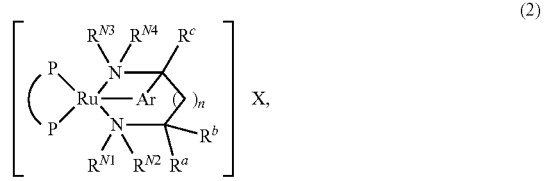

wherein

represents an optically active diphosphine; X represents an anionic group; $R^a$, $R^b$, and $R^c$ each independently represent a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; $R^{N1}$ and $R^a$ may together form an optionally substituted alkylene group; n represents an integer of 0 to 3; and Ar represents an optionally substituted arylene group.

2. The production method according to claim 1, wherein the ruthenium complex is of the following general formula (3) or (4):

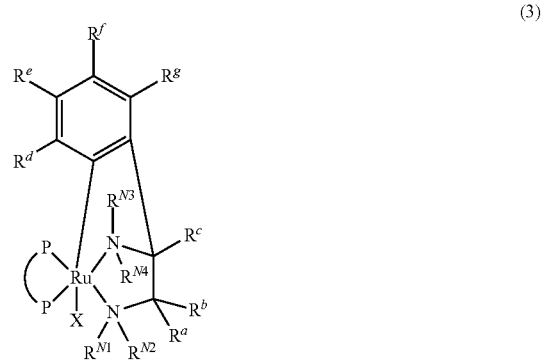

-continued

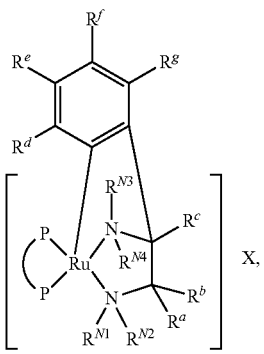
(4)

wherein

represents an optically active diphosphine; X represents an anionic group; $R^a$, $R^b$, and $R^c$ each independently represent a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^d$, $R^e$, $R^f$, and $R^g$ each independently represent a hydrogen atom, an optionally substituted $C_1$ to $C_{20}$ alkyl group, a $C_1$ to $C_5$ halogenated alkyl group, a halogen atom, an optionally substituted aryl group, an optionally substituted $C_3$ to $C_8$ cycloalkyl group, a tri-substituted silyl group, or an optionally substituted $C_1$ to $C_{20}$ alkoxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; and $R^{N1}$ and $R^a$ may together form an optionally substituted alkylene group.

3. The production method according to claim 1, wherein the optically active diphosphine represented by

is a diphosphine of the following general formula (5):

$$R^1R^2P\text{-}Q\text{-}PR^3R^4 \qquad (5),$$

wherein $R^1$, $R^2$, $R^3$, and $R^4$ each independently represent an optionally substituted aryl group, an optionally substituted cycloalkyl group, or an optionally substituted alkyl group, and the pair of $R^1$ and $R^2$ and/or the pair of $R^3$ and $R^4$ may together form a ring; and Q represents biphenyldiyl, binaphthalenediyl, bipyridinediyl, paracyclophanediyl, or ferrocenediyl group, has an asymmetric structure, and may be substituted.

4. The production method according to claim 2, wherein the optically active diphosphine represented by

is a diphosphine of the following general formula (5):

$$R^1R^2P\text{-}Q\text{-}PR^3R^4 \qquad (5),$$

wherein $R^1$, $R^2$, $R^3$, and $R^4$ each independently represent an optionally substituted aryl group, an optionally substituted cycloalkyl group, or an optionally substituted alkyl group, and the pair of $R^1$ and $R^2$ and/or the pair of $R^3$ and $R^4$ may together form a ring; and Q represents biphenyldiyl, binaphthalenediyl, bipyridinediyl, paracyclophanediyl, or ferrocenediyl group, has an asymmetric structure, and may be substituted.

5. The production method according to claim 3, wherein the

is an optically active diphosphine of the following general formula (6):

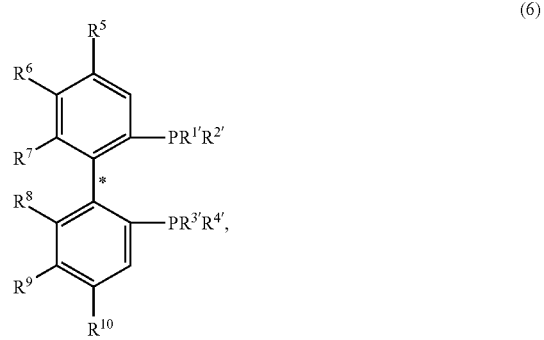
(6)

wherein $R^{1'}$, $R^{2'}$, $R^{3'}$, and $R^{4'}$ each independently represent a phenyl group optionally substituted by a substituent(s) selected from the group consisting of alkyl groups having 1 to 4 carbon atoms and alkoxy groups having 1 to 4 carbon atoms; a cyclopentyl group; or a cyclohexyl group; $R^5$, $R^6$, $R^7$, $R^8$, $R^9$, and $R^{10}$ each independently represent a hydrogen atom, an optionally substituted alkyl group having 1 to 4 carbon atoms, an optionally substituted alkoxy group having 1 to 4 carbon atoms, a halogen atom, a halogenated alkyl group having 1 to 4 carbon atoms, or a dialkylamino group, or two of $R^5$, $R^6$, and $R^7$ may together form an optionally substituted alkylene group; an optionally substituted alkylenedioxy group; or an optionally substituted aromatic ring, two of $R^8$, $R^9$, and $R^{10}$ may together form an optionally substituted alkylene group; an optionally substituted alkylenedioxy group; or an optionally substituted aromatic ring, $R^7$ and $R^8$ may together form an optionally substituted alkylene group; an optionally substituted alkylenedioxy group; or an optionally substituted aromatic ring, provided that neither $R^7$ nor $R^8$ is a hydrogen atom; and * indicates axial chirality.

6. The production method according to claim 4, wherein the

is an optically active diphosphine of the following general formula (6):

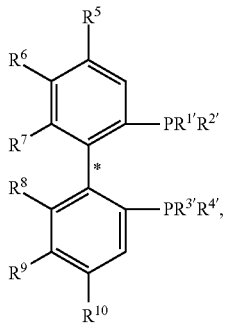

(6)

wherein $R^{1'}$, $R^{2'}$, $R^{3'}$, and $R^{4'}$ each independently represent a phenyl group optionally substituted by a substituent(s) selected from the group consisting of alkyl groups having 1 to 4 carbon atoms and alkoxy groups having 1 to 4 carbon atoms; a cyclopentyl group; or a cyclohexyl group; $R^5$, $R^6$, $R^7$, $R^8$, $R^9$, and $R^{10}$ each independently represent a hydrogen atom, an optionally substituted alkyl group having 1 to 4 carbon atoms, an optionally substituted alkoxy group having 1 to 4 carbon atoms, a halogen atom, a halogenated alkyl group having 1 to 4 carbon atoms, or a dialkylamino group, or two of $R^5$, $R^6$, and $R^7$ may together form an optionally substituted alkylene group; an optionally substituted alkylenedioxy group; or an optionally substituted aromatic ring, two of $R^8$, $R^9$, and $R^{10}$ may together form an optionally substituted alkylene group; an optionally substituted alkylenedioxy group; or an optionally substituted aromatic ring, $R^7$ and $R^8$ may together form an optionally substituted alkylene group; an optionally substituted alkylenedioxy group; or an optionally substituted aromatic ring, provided that neither $R^7$ nor $R^8$ is a hydrogen atom; and * indicates axial chirality.

7. The production method according to claim 3, wherein $R^1$, $R^2$, $R^3$, and $R^4$ in general formula (5) are 3,5-xylyl groups.

8. The production method according to claim 4, wherein $R^1$, $R^2$, $R^3$, and $R^4$ in general formula (5) are 3,5-xylyl groups.

9. The production method according to claim 5, wherein $R^{1'}$, $R^{2'}$, $R^{3'}$, and $R^{4'}$ in general formula (6) are 3,5-xylyl groups.

10. The production method according to claim 6, wherein $R^{1'}$, $R^{2'}$, $R^{3'}$, and $R^{4'}$ in general formula (6) are 3,5-xylyl groups.

11. The production method according to claim 1, wherein the method is conducted in the presence of a base compound.

12. A method for producing an optically active amine compound of the formula (H), comprising:
performing an asymmetric hydrogenation of a 2H-1,4-benzoxazine derivative or a 2H-1,4-benzothiazine derivative of the formula (G) in the presence of a ruthenium complex of the general formula (1) or (2):

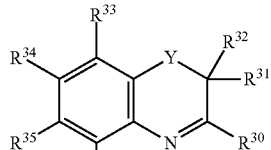

(G)

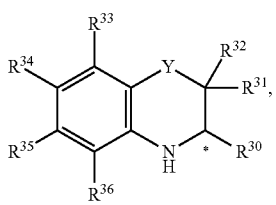

(H)

wherein Y represents an oxygen atom or a sulfur atom, $R^{30}$, $R^{31}$, $R^{32}$, $R^{33}$, $R^{34}$, $R^{35}$, and $R^{36}$ each independently represent a hydrogen atom, a halogen atom, an optionally substituted alkyl group, an optionally substituted (hetero)aryl group, an optionally substituted $C_3$ to $C_8$ cycloalkyl group, a tri-substituted silyl group, an optionally substituted alkoxy group, or an optionally substituted aralkyl group; * indicates an asymmetric carbon; and when $R^{31}$ and $R^{32}$ are the same substituents, the carbon atom to which $R^{31}$ and $R^{32}$ are bound is not an asymmetric carbon,

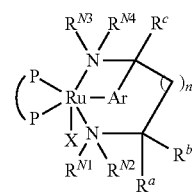

(1)

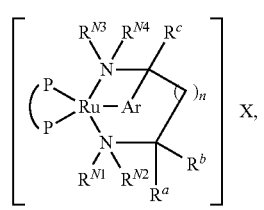

(2)

wherein

represents an optically active diphosphine; X represents an anionic group; $R^a$, $R^b$, and $R^c$ each independently represent a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclic group, or $R^b$ and $R^c$ may together form an optionally substituted alkylene group or an optionally substituted alkylenedioxy group; $R^{N1}$, $R^{N2}$, $R^{N3}$, and $R^{N4}$ each independently represent a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$, and $R^{N4}$ is a hydrogen atom; $R^{N1}$ and $R^a$ may together form an optionally substituted alkylene group; n represents an integer of 0 to 3; and Ar represents an optionally substituted arylene group.

* * * * *